US 10,136,801 B2

(12) United States Patent
Tanii

(10) Patent No.: US 10,136,801 B2
(45) Date of Patent: Nov. 27, 2018

(54) BENDING PORTION AND ENDOSCOPE

(71) Applicant: OLYMPUS CORPORATION, Tokyo (JP)

(72) Inventor: Yoshiyuki Tanii, Hamura (JP)

(73) Assignee: OLYMPUS CORPORATION, Tokyo (JP)

(*) Notice: Subject to any disclaimer, the term of this patent is extended or adjusted under 35 U.S.C. 154(b) by 252 days.

(21) Appl. No.: 14/175,474

(22) Filed: Feb. 7, 2014

(65) Prior Publication Data
US 2014/0180009 A1 Jun. 26, 2014

Related U.S. Application Data

(63) Continuation of application No. PCT/JP2012/081632, filed on Dec. 6, 2012.

(30) Foreign Application Priority Data

Dec. 6, 2011 (JP) .................. 2011-267275
Dec. 6, 2011 (JP) .................. 2011-267276
Dec. 6, 2011 (JP) .................. 2011-267277

(51) Int. Cl.
A61B 1/00 (2006.01)
A61B 1/008 (2006.01)
(Continued)

(52) U.S. Cl.
CPC ............ *A61B 1/008* (2013.01); *A61B 1/0011* (2013.01); *A61B 1/0055* (2013.01); *G02B 23/2476* (2013.01); *F04C 2270/0421* (2013.01)

(58) Field of Classification Search
CPC .. A61B 1/0055; A61B 1/008; A61M 25/0013; A61M 25/0015
(Continued)

(56) References Cited

U.S. PATENT DOCUMENTS 5,807,241 A * 9/1998 Heimberger ......... A61B 1/0055
600/139
6,656,195 B2 * 12/2003 Peters et al. .................. 606/159
(Continued)

FOREIGN PATENT DOCUMENTS

EP 0 626 604 A2 11/1994
EP 0764423 A1 3/1997
(Continued)

OTHER PUBLICATIONS

International Search Report dated Feb. 19, 2013 issued in PCT/JP2012/081632.
(Continued)

*Primary Examiner* — Alexandra L Newton
*Assistant Examiner* — Rynae Boler
(74) *Attorney, Agent, or Firm* — Scully, Scott, Murphy & Presser, P.C.

(57) ABSTRACT

A bending portion includes: a bending piece set in which a plurality of bending pieces are continuously provided by forming a convex portion on a first bending piece and a concave portion on a second bending piece by cutting a rigid pipe, the convex portion and the concave portion forming an engagement portion that pivotably couples adjacent bending pieces to each other, wherein a first engagement portion includes: a first convex portion formed on the first bending piece and including a first peripheral portion serving as a first pivoting surface; and a first concave portion formed on the second bending piece and including a first inner circumferential portion on which the first peripheral portion slides, and the first engagement portion has, in the first peripheral portion, a tapered surface having an outer diameter that becomes smaller from a bending piece inner surface side toward a bending piece outer surface side.

10 Claims, 15 Drawing Sheets

(51) Int. Cl.
*A61B 1/005* (2006.01)
*G02B 23/24* (2006.01)

(58) Field of Classification Search
USPC .............................. 600/142; 604/95.04, 528
See application file for complete search history.

(56) References Cited

U.S. PATENT DOCUMENTS

2005/0272978 A1* 12/2005 Brunnen et al. .............. 600/142
2007/0233043 A1* 10/2007 Dayton et al. ................ 604/526
2008/0287741 A1* 11/2008 Ostrovsky et al. ........... 600/141

FOREIGN PATENT DOCUMENTS

| JP | 09-117413 A | 5/1997 |
| JP | 09-154806 A | 6/1997 |
| JP | 09-299317 A | 11/1997 |
| WO | 2011/080104 A1 | 7/2011 |

OTHER PUBLICATIONS

Extended Supplementary European Search Report dated Mar. 6, 2015 from related European Application No. 12 85 6383.0.

* cited by examiner

BENDING PORTION AND ENDOSCOPE

CROSS REFERENCE TO RELATED APPLICATION

This application is a continuation application of PCT/JP2012/081632 filed on Dec. 6, 2012 and claims benefit of Japanese Applications No. 2011-267275 filed in Japan on Dec. 6, 2011, No. 2011-267276 filed in Japan on Dec. 6, 2011 and No. 2011-267277 filed in Japan on Dec. 6, 2011, the entire contents of which are incorporated herein by this reference.

BACKGROUND OF THE INVENTION

1. Field of the Invention

The present invention relates to a bending portion including a bending piece set that includes a plurality of bending pieces formed by cutting a rigid pipe and is configured by pivotably coupling adjacent bending pieces to each other.

2. Description of the Related Art

Endoscopes applicable to industrial use and medical use are each provided with an insertion portion to be inserted into a living body or a tube. In general, in such an endoscope including a flexible insertion portion, a bending portion is provided on a distal end side of the insertion portion. The bending portion performs a bending action along with an operation of an operation apparatus provided to an operation portion. Accordingly, in the endoscope including the bending portion, the operation apparatus enables an observation portion provided in a distal end portion to face in a desired direction.

The bending portion is provided with a bending piece set. The bending piece set is configured by pivotably coupling a plurality of bending pieces to each other such that the bending piece set is bent at a predetermined angle in a predetermined direction. In general, the plurality of bending pieces constituting the bending piece set are pivotably coupled to each other by pivot pins.

Japanese Patent Application Laid-Open Publication No. 09-117413 discloses an inflectable tube as a barrel for a flexible endoscope that can be simply and economically made, and also discloses a manufacturing method therefor. The inflectable tube (corresponding to a bending portion set in the invention of the present application) is formed by laser-cutting a rigid tube. As illustrated in FIG. 1A (corresponding to FIG. 4 in Japanese Patent Application Laid-Open Publication No. 09-117413), adjacent tube part 2*a* (indicated by solid lines) and tube part 2*b* (indicated by broken lines) of an inflectable tube 1 formed by laser-cutting are separated from each other by a circumferential separation joint in terms of a material. On the other hand, the adjacent tube part 2*a* and tube part 2*b* of the inflectable tube 1 are reliably connected to each other by an engagement portion 3 formed by the separation joint.

Then, the tube parts 2*a*, 2*b* of the inflectable tube 1 pivot with respect to each other about the engagement portion 3 including a circular convex portion 3*b* and a circular concave portion 3*c*, so that the tube part 2*b* is inflected by θ1 with respect to the tube part 2*a*, for example, as indicated by chain double-dashed lines (corresponding to FIG. 6 in Japanese Patent Application Laid-Open Publication No. 09-117413). In the figure, the tube part 2*a* and the tube part 2*b* have the same shape.

Note that, in the present embodiment, the inflectable tube is also described as bending portion set, and each tube part is also described as bending piece.

There is a significant difference in tensile strength between: the bending portion set in which the adjacent bending pieces are connected to each other by the engagement portion as described above; and the bending portion set in which the adjacent bending pieces are coupled to each other by the pivot pins such as rivets as described above. More specifically, the bending portion set in which the bending pieces are coupled to each other by the pivot pins is higher in tensile strength than the bending portion set in which the bending pieces are connected to each other by the engagement portion.

For this reason, the bending portion including the bending portion set in which the bending pieces are coupled to each other by the pivot pins is higher in resistance to tensile stress. Accordingly, a technique of pulling a sigmoid colon or a transverse colon closer by means of the insertion portion inserted in a large intestine can be easily performed. Moreover, when the insertion portion is cleaned and disinfected, the bending portion is drawn through an operator's hand in an insertion direction, whereby the cleaning work can be easily performed.

Moreover, in the endoscope including the bending portion in the insertion portion, the bending portion is required to be capable of turning in a small circle, in addition to a reduction in diameter of the insertion portion. The bending portion capable of turning in a small circle refers to a bending portion having a small bending radius at the time of bending and having a small length. In the endoscope including the bending portion capable of turning in a small circle, if a bending action of the bending portion is performed with a forward region in the insertion direction being observed, for example, observation up to a rearward region in the insertion direction is possible.

In the bending portion set in Japanese Patent Application Laid-Open Publication No. 09-117413, as illustrated in FIG. 1B, an inflection angle between neighboring bending pieces 2Aa, 2Ab constituting a bending portion set 1A is set to an angle θ2 larger than the angle θ1 illustrated in FIG. 1A. For this reason, in each bending piece 2A in FIG. 1B, an end face position of a first escape portion 4 and an end face position of a second escape portion 5 that are provided to each bending piece 2 in FIG. 1A are respectively changed from first positions 4*a*, 5*a* to second positions 4*b*, 5*b*. As a result, as illustrated in FIG. 2, a bending radius of the bending portion set 1A is smaller than a bending radius of the bending portion set 1.

Moreover, in a bending portion set 1B illustrated in FIG. 1C, a distance between pivot axes of neighboring bending pieces 2Ba, 2Bb is set to a length L2 smaller than a length L1 illustrated in FIG. 1A. For this reason, each bending piece 2B of the bending portion set 1B corresponds to one formed by omitting, for example, middle parts 6*a*, 6*b* that are indicated by hatched lines in the bending piece 2 constituting the bending portion set 1. As a result, as illustrated in FIG. 2, a bending radius of the bending portion set 1B is smaller than the bending radius of the bending portion set 1.

Further, a bending portion set 1C is configured such that a distance between pivot axes of neighboring bending pieces 2Ca, 2Cb is set to L2 and that the neighboring bending pieces 2Ca, 2Cb pivot with respect to each other at the angle θ2 as illustrated in FIG. 1D. Consequently, a length of the bending piece set can be made smaller, and, as illustrated in FIG. 2, a bending radius of the bending portion set 1C is smaller than the bending radii of the bending portion sets 1, 1A, 1B.

In the bending portion sets 1, 1A, 1B, 1C in each of which the bending pieces are connected to each other by the engagement portion, as illustrated in FIG. 3, the engagement portion 3 including the circular convex portion 3b and the circular concave portion 3c is configured by a separation joint 9 formed by a laser beam. The separation joint 9 is formed by the laser beam that is applied from an outer circumferential face side of a rigid pipe 8 toward a central axis 8a of the pipe 8. For this reason, in the engagement portion 3, a convex-portion tapered surface 3Tb formed in a periphery of the circular convex portion 3b is put on a concave-portion tapered surface 3Tc formed in an inner circumference of the circular concave portion 3c.

SUMMARY OF THE INVENTION

An bending portion according to an aspect of the present invention includes a bending piece set in which a plurality of bending pieces are pivotably continuously provided, the plurality of bending pieces being formed simultaneously by cutting a rigid pipe while a convex portion is formed on a first bending piece and a concave portion is formed on a second bending piece simultaneously, the convex portion and the concave portion forming an engagement portion that pivotably couples adjacent bending pieces to each other, wherein a first engagement portion includes: a first convex portion formed on the first bending piece and including a first peripheral portion serving as a first pivoting surface; and a first concave portion formed on the second bending piece and including a first inner circumferential portion on which the first peripheral portion of the first convex portion slides, the first convex portion and the first concave portion being formed simultaneously, and the first engagement portion has a tapered surface in the first peripheral portion of the first convex portion, the tapered surface having an outer diameter that becomes smaller from a bending piece inner surface side toward a bending piece outer surface side.

An endoscope according to one aspect of the present invention includes a bending portion provided at a distal end side of the insertion portion configured to be inserted into a living body or a tube, and the bending portion is provided with a bending piece set in which a plurality of bending pieces are pivotably continuously provided, the plurality of bending pieces being formed simultaneously by cutting a rigid pipe while a convex portion is formed on a first bending piece and a concave portion is formed on a second bending piece simultaneously, the convex portion and the concave portion forming an engagement portion that pivotably couples adjacent bending pieces to each other; wherein a first engagement portion includes: a first convex portion formed on the first bending piece and including a first peripheral portion serving as a first pivoting surface; and a first concave portion formed on the second bending piece and including a first inner circumferential portion on which the first peripheral portion of the first convex portion slides, the first convex portion and the first concave portion being formed simultaneously, and the first engagement portion has a tapered surface in the first peripheral portion of the first convex portion, the tapered surface having an outer diameter that becomes smaller from a bending piece inner surface side toward a bending piece outer surface side.

DETAILED DESCRIPTION OF THE PREFERRED EMBODIMENTS

Hereinafter, a first embodiment of the present invention is described with reference to the drawings.

The first embodiment of the present invention is described with reference to FIG. 4 to FIG. 9.

Figure 1A:
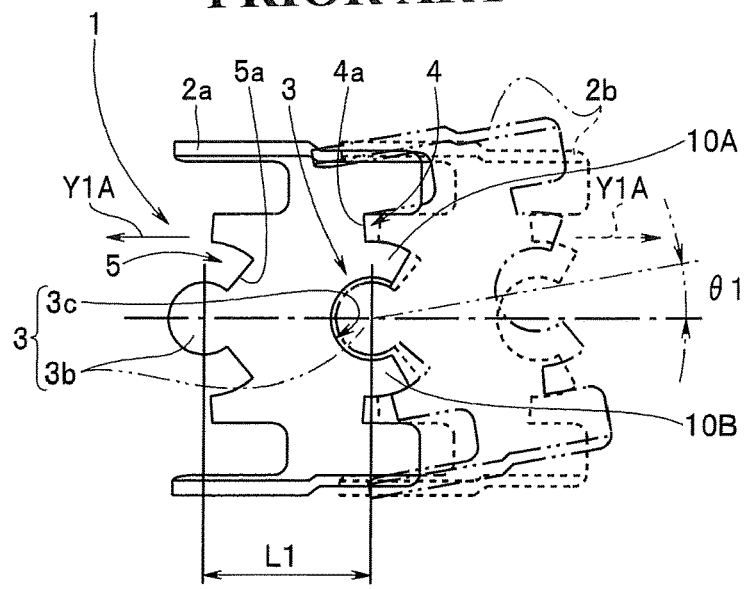
FIG. 1A is a view for describing a configuration of adjacent tube parts of a conventional inflectable tube.
Figure 1B:
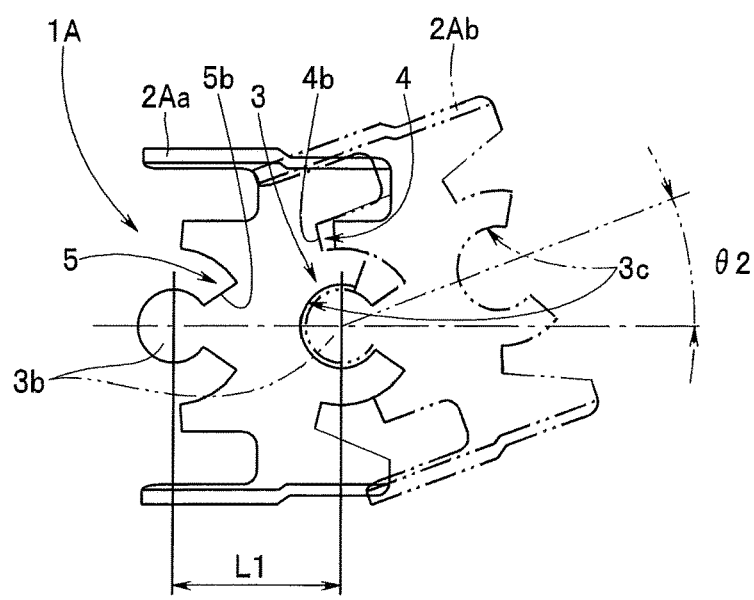
FIG. 1B is a view for describing an inflectable tube in which an inflection angle between adjacent bending pieces is set to an angle θ2 larger than an angle θ1 in FIG. 1A.
Figure 1C:
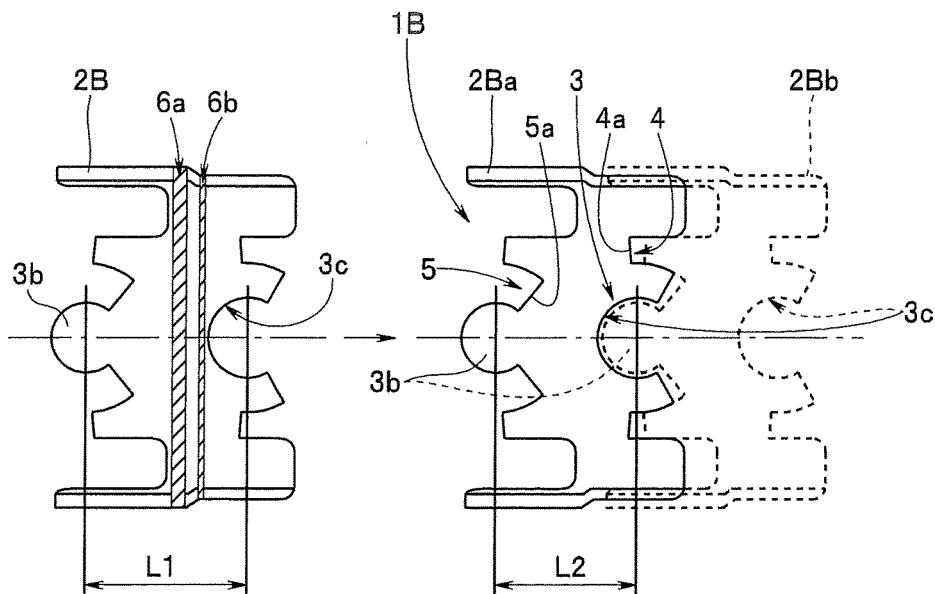
FIG. 1C is a view for describing an inflectable tube in which a distance between pivot axes of adjacent bending pieces is set to a length L2 smaller than a length L1 in FIG. 1A.
Figure 1D:
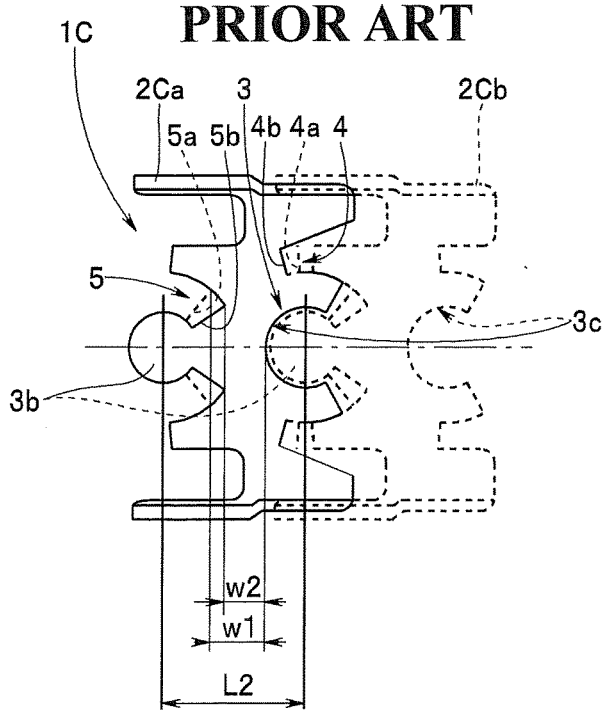
FIG. 1D is a view for describing an inflectable tube in which a distance between pivot axes of adjacent bending pieces is set to the length L2 and an inflection angle between the adjacent bending pieces is set to the angle θ2.
Figure 2:
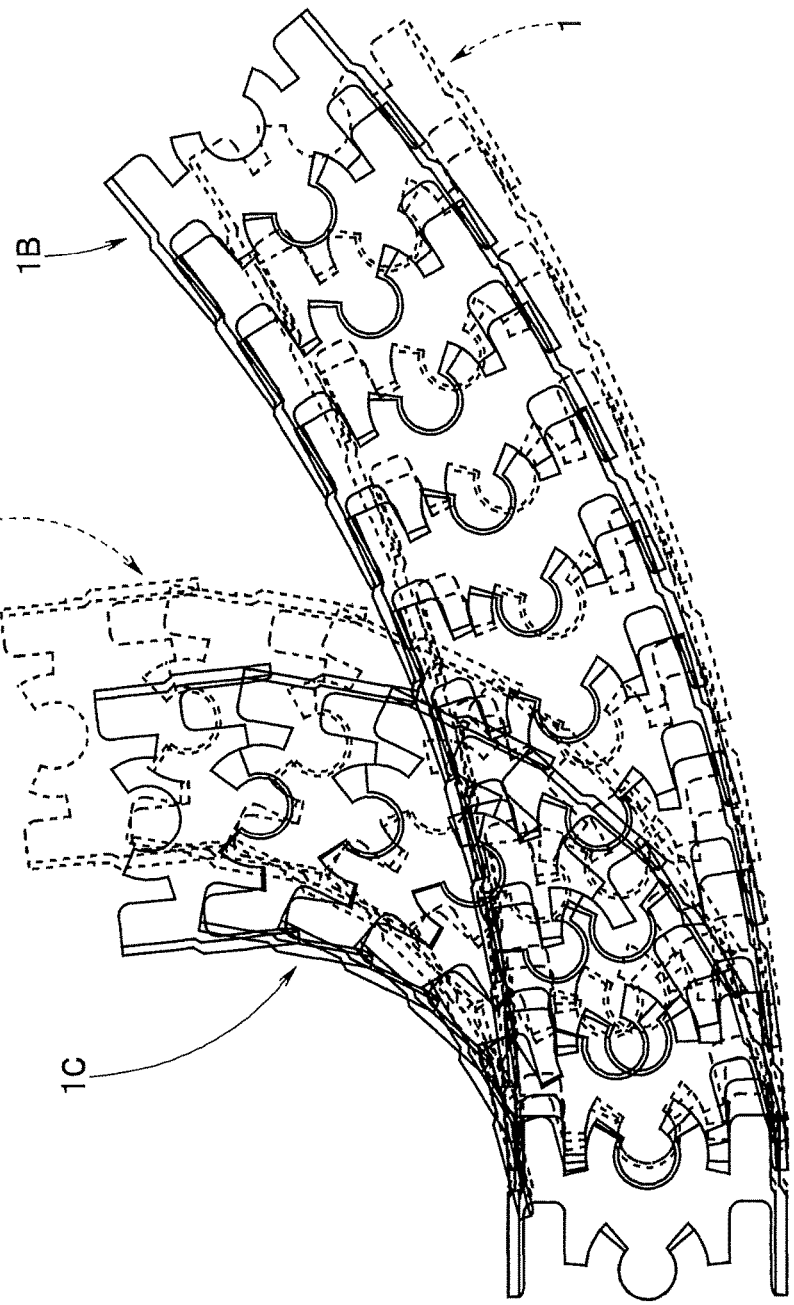
FIG. 2 is a view for comparison among: a bending radius of the conventional inflectable tube; a bending radius of the inflectable tube in which the distance between the pivot axes of the adjacent bending pieces is set to the length L2; a bending radius of the inflectable tube in which the inflection angle between the adjacent bending pieces is set to the angle θ2; and a bending radius of the inflectable tube in which the distance between the pivot axes of the adjacent bending pieces is set to the length L2 and the inflection angle between the adjacent bending pieces is set to the angle θ2.
Figure 3:
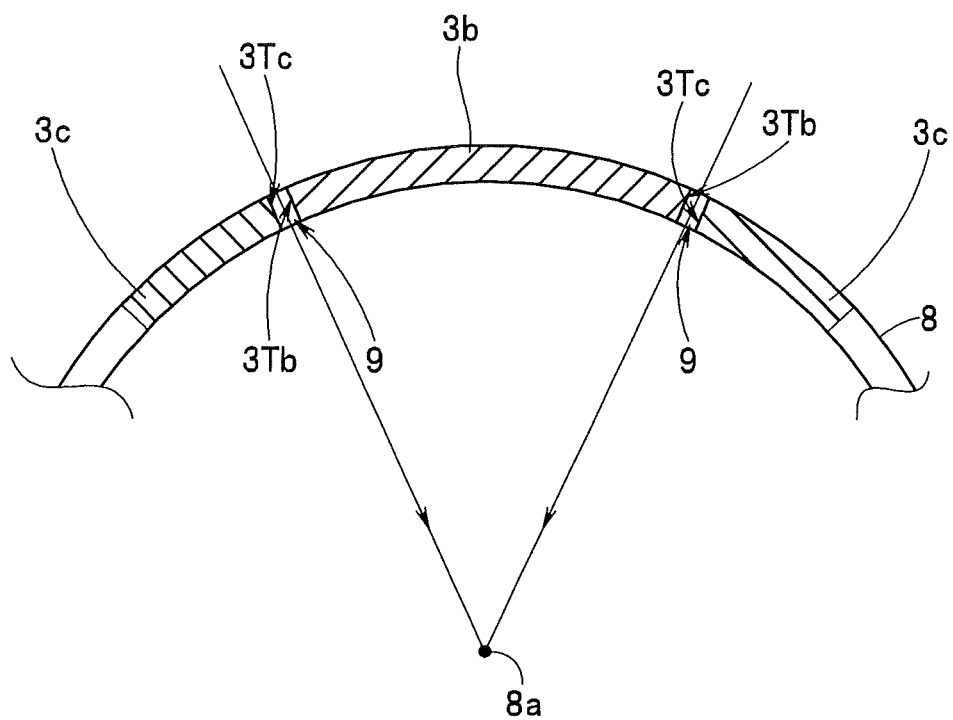
FIG. 3 is a schematic view for describing tapered surfaces that are formed on a rigid pipe by a laser beam as well as a relation between a circular convex portion and a circular concave portion.
Figure 4:
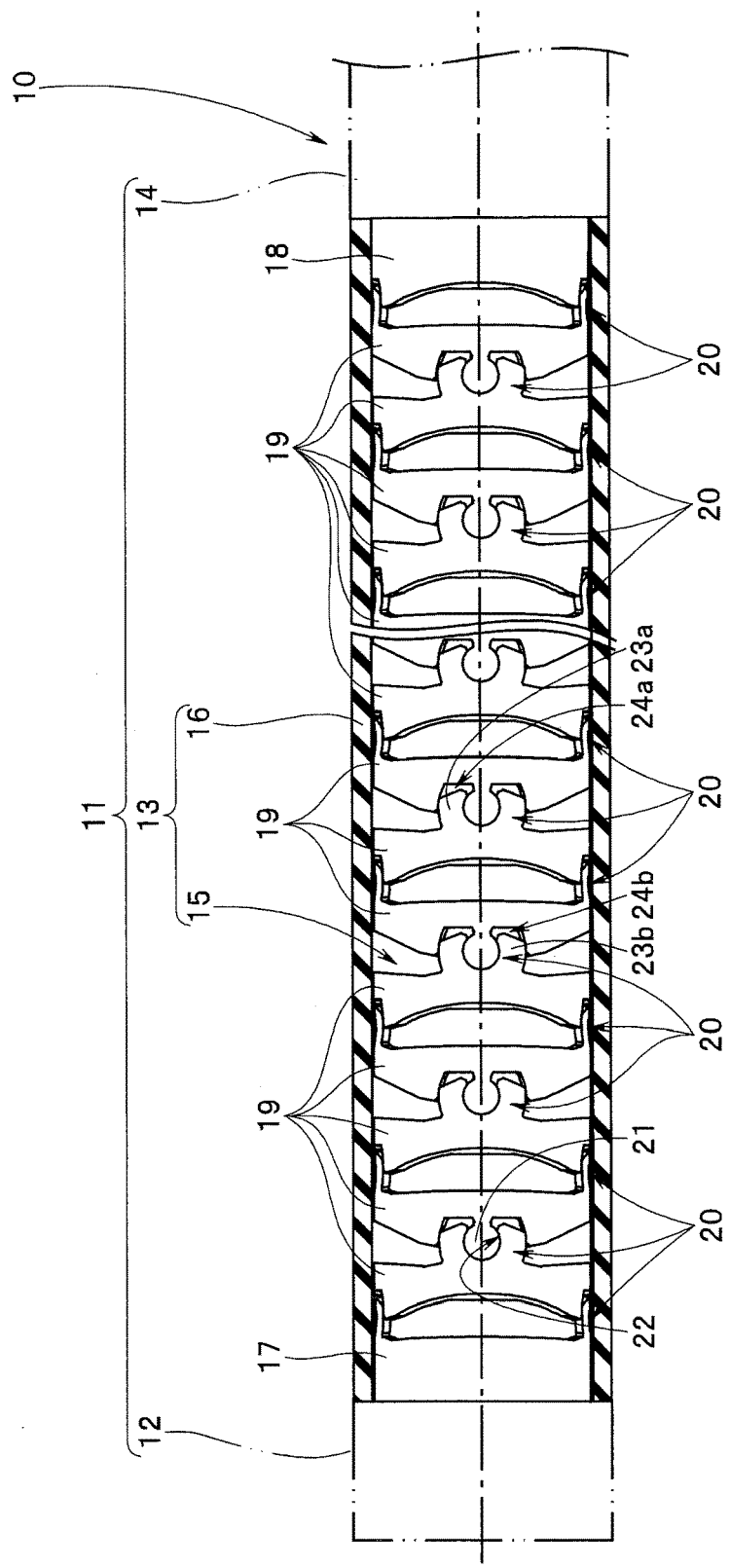
FIG. 4 is a view for describing an endoscope including a bending portion including a bending piece set having a configuration in which: a plurality of bending pieces that are formed by applying a laser beam from an outer circumferential face side of a rigid pipe are pivotably continuously provided; and a reduction in length and a reduction in radius are thus achieved, according to a first embodiment of the present invention.
Figure 5:
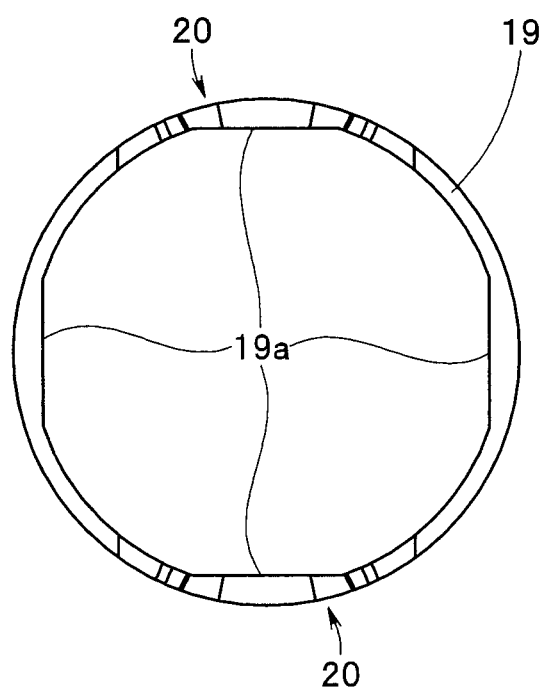
FIG. 5 is a view of middle bending pieces in FIG. 6, which are observed in an arrow Y5 direction.

As illustrated in FIG. 4, an insertion portion 11 of an endoscope 10 includes a distal end portion 12, a bending portion 13, and a flexible tube portion 14 that are continuously provided. The bending portion 13 includes a bending piece set 15 and a bending portion cover 16. The bending portion cover 16 covers an outer circumferential face of the bending piece set 15. The bending portion cover 16 is made of an elastic resin or rubber. In the present embodiment, the bending portion 13 is bent in four directions, that is, a top-bottom direction and a left-right direction.

Note that a braided net may be interposed between the bending piece set 15 and the bending portion cover 16 constituting the bending portion 13.

The bending piece set 15 includes a distal end bending piece 17, a proximal end bending piece 18, and a plurality of middle bending pieces 19. In the present embodiment, the distal end bending piece 17, the plurality of middle bending pieces 19, and the proximal end bending piece 18 constituting the bending piece set 15 are formed by cutting one rigid pipe (not illustrated) through application of a laser beam from an outer circumferential face side of the rigid pipe.

In the present embodiment, when the distal end bending piece 17 and the middle bending piece 19 adjacent thereto are cut, engagement portions 20 are formed. The engagement portions 20 are separation joints that pivotably engage the distal end bending piece 17 and the middle bending piece 19 with each other without disengagement therebetween. Similarly, when the adjacent middle bending pieces 19 are cut and when the middle bending piece 19 and the proximal end bending piece 18 adjacent thereto are cut, the engagement portions 20 that pivotably couple the adjacent bending pieces to each other without disengagement therebetween are formed. As a result, the bending piece set 15 including the distal end bending piece 17, the plurality of middle bending pieces 19, and the proximal end bending piece 18 that are pivotably coupled to each other is formed from the one rigid pipe.

Figure 6:
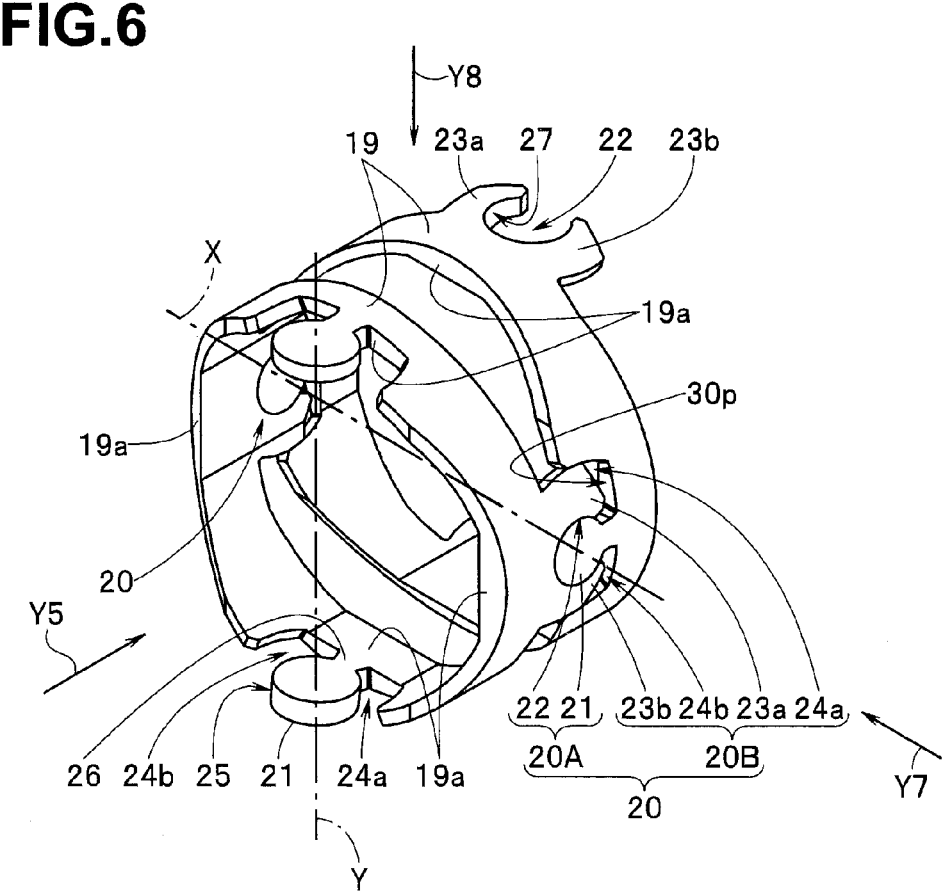
FIG. 6 is a view for describing a configuration of the adjacent middle bending pieces that are coupled to each other by engagement portions so as to be pivotable in a top-bottom direction and a left-right direction, and reinforcing portions of the bending pieces.

The bending piece set 15 is configured by processing a straight rigid pipe in which a thickness of a part corresponding to each engagement portion 20 is larger than a thickness therearound. That is, each middle bending piece 19 has a cross-sectional shape illustrated in FIG. 5. As illustrated in FIG. 6, a thickness of the middle bending piece 19 is uneven, and thick portions 19a are provided at regular intervals in a circumferential direction. Then, the engagement portions 20 are respectively formed in the thick portions 19a.

Note that the bending piece set 15 may be configured by processing a straight rigid pipe having an even diameter size. Moreover, the rigid pipe is not limited to a straight shape, and may be a stepped pipe in which a diameter size on a pipe distal end side, a diameter size on a pipe proximal end side, and a diameter size in a pipe middle part between the distal end-side portion and the proximal end-side portion are different. Examples of the stepped pipe include: a pipe in which the diameter sizes on the distal end side and the proximal end side are the same and the diameter size in the middle part is larger or smaller; and a pipe in which the diameter size is larger or smaller in order of the distal end side, the middle part, and the proximal end side.

A configuration of the engagement portions 20 that pivotably couple the adjacent middle bending pieces 19 to each other is described with reference to FIG. 4 and FIG. 6 to FIG. 8.

In the bending piece set 15 formed by cutting the rigid pipe according to the present embodiment, a distance between the engagement portions 20 and the engagement portions 20 of the adjacent bending pieces, that is, a distance between pivot axes thereof is set to a predetermined size, for the purpose of achieving a reduction in length of the bending portion 13. Moreover, a maximum bending angle between the adjacent bending pieces is set to a predetermined angle, for the purpose of achieving a reduction in bending radius of the bending portion 13.

The neighboring bending pieces illustrated in FIG. 4 are pivotably coupled to each other by the engagement portions 20. Then, a configuration of the engagement portions 20 that pivotably couple the distal end bending piece 17 and the middle bending piece 19 adjacent to the piece 17 and a configuration of the engagement portions 20 that pivotably couple the middle bending piece 19 and the proximal end bending piece 18 are substantially the same as a configuration of the engagement portions 20 that pivotably couple the middle bending pieces 19 to each other.

Accordingly, in the following description, a configuration of the adjacent middle bending pieces 19 is described, and description of the distal end bending piece 17 and the proximal end bending piece 18 is simplified.

Figure 7:
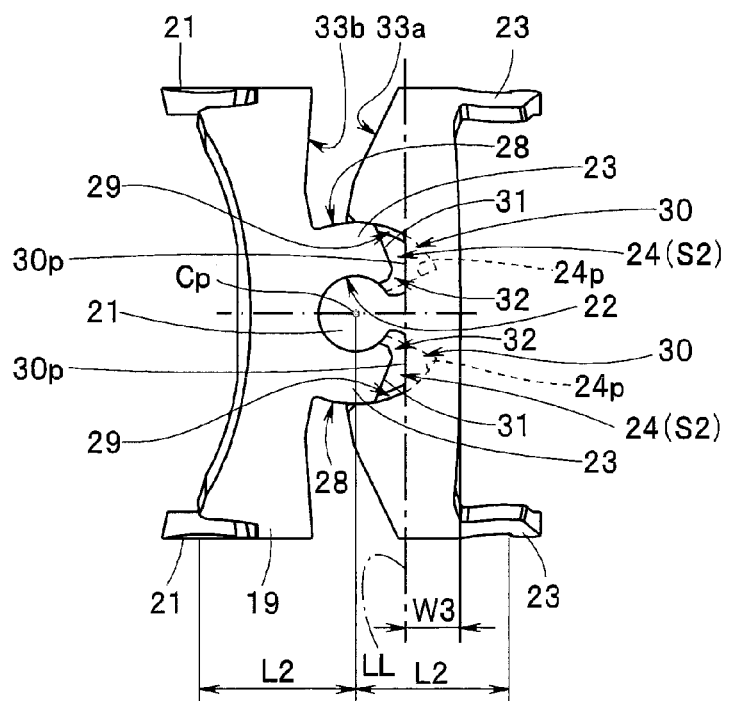
FIG. 7 is a side view of the adjacent middle bending pieces in FIG. 6, which are observed in an arrow Y7 direction.
Figure 8:
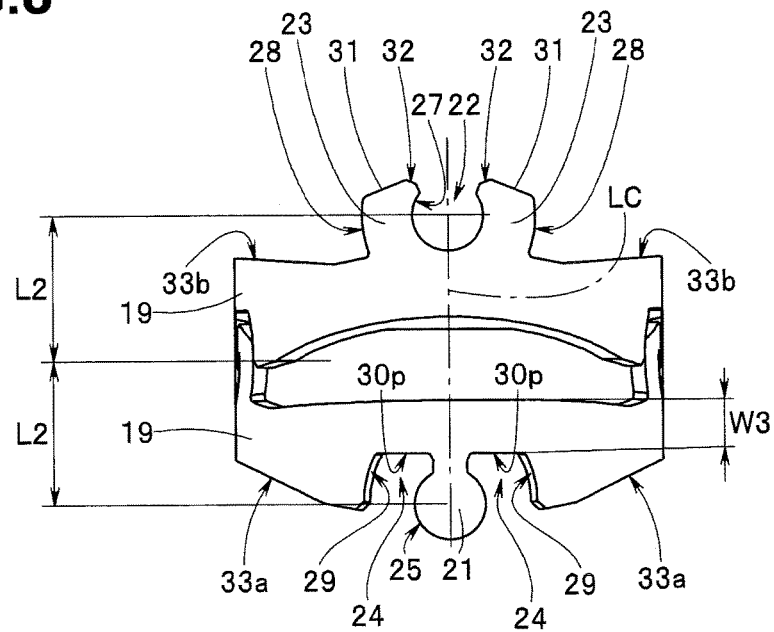
FIG. 8 is a top view of the adjacent middle bending pieces in FIG. 6, which are observed in an arrow Y8 direction.
Figure 9:
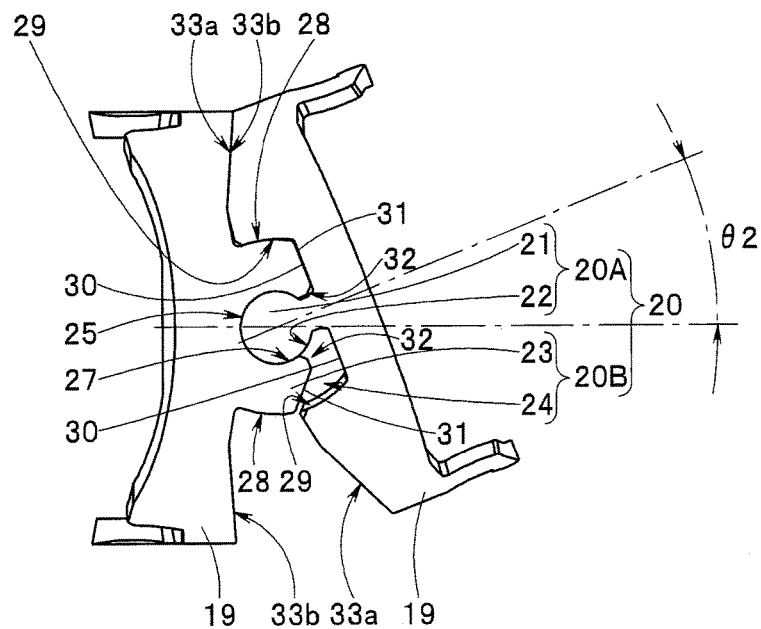
FIG. 9 is a view for describing a state where the adjacent middle bending pieces are maximally bent.

In the present embodiment, as illustrated in FIG. 6, the adjacent middle bending pieces 19 pivot with respect to each other in, for example, the top-bottom direction about an axis X passing through centers of the engagement portions 20. On the other hand, the middle bending pieces 19 pivot with respect to each other in the left-right direction about an axis Y orthogonal to the axis X. Then, as illustrated in FIG. 7 and FIG. 8, a distance between the engagement portions 20 having the axis X and the engagement portions having the axis Y is set to a predetermined size L2. Moreover, when a distal end-side contact surface denoted by reference sign 33a and a proximal end-side contact surface denoted by reference sign 33b come into contact with each other, the adjacent middle bending pieces 19 are in a maximum bent state illustrated in FIG. 9 and at a predetermined bending angle θ2.

As illustrated in FIG. 6, each engagement portion 20 includes a first engagement portion 20A and a second engagement portion 20B. The first engagement portion 20A includes a first convex portion denoted by reference sign 21 and a first concave portion denoted by reference sign 22. The second engagement portion 20B includes a pair of second convex portions denoted by reference signs 23a, 23b and a pair of second concave portions denoted by reference signs 24a, 24b.

The first convex portion 21 includes a first peripheral portion 25 serving as a first pivoting surface and a support portion 26. On the other hand, the first concave portion 22 includes a first inner circumferential portion 27 that is opposed to the first peripheral portion 25 to serve as a sliding surface.

Then, a central line connecting centers of the first convex portions 21 provided to one of the adjacent middle bending pieces 19 and a central line connecting centers of the first concave portions 22 provided to the other of the adjacent middle bending pieces 19 are orthogonal to a central axis of the rigid pipe for forming the bending piece set 15. Then, in a state where each first convex portion 21 engages with each first concave portion 22, the center of the first convex portion 21 is coincident with the center of the first concave portion 22.

As illustrated in FIG. 4 and FIG. 6, the pair of second convex portions 23a, 23b are formed on a proximal end side of the middle bending piece 19 so as to sandwich the first concave portion 22. The second convex portion 23a on one side and the second convex portion 23b on the other side have shapes symmetrical to a straight line that passes through the center of the first concave portion 22 and is parallel to the central axis of the rigid pipe. Moreover, the pair of second concave portions 24a, 24b are formed on a distal end side of the middle bending piece 19 so as to sandwich the first convex portion 21. The second concave portion 24a on one side and the second concave portion 24b on the other side have shapes symmetrical to a straight line that passes through the center of the first convex portion 21 and is parallel to the central axis of the rigid pipe.

Two first convex portions 21 and two pairs of second concave portions 24a, 24b are provided on a distal end bending piece side (hereinafter, described as distal end side) of the middle bending piece 19 so as to be opposed to each other. Two first concave portions 22 and two pairs of second convex portions 23a, 23b are provided on a proximal end bending piece side (hereinafter, described as proximal end side) of the middle bending piece 19 so as to be opposed to each other. In other words, concave locking portions are provided on the distal end side of one middle bending piece 19 so as to be opposed to each other, and the concave locking portions are distal end-side locking portions each including the second concave portion 24a and the second concave portion 24b that sandwich the first convex portion 21. On the other hand, convex locking portions are provided on the proximal end side of one middle bending piece 19 so as to be opposed to each other, and the convex locking portions are proximal end-side locking portions each including the second convex portion 23a and the second convex portion 23b that sandwich the first concave portion 22, the proximal end-side locking portions respectively engaging with the concave locking portions.

The first convex portion 21 and the first concave portion 22, the second convex portion 23a and the second concave portion 24a, and the second convex portion 23b and the second concave portion 24b are respectively formed at the same time by cutting with a laser beam. Note that the cutting with a laser beam is described later.

In the following description, the pair of second convex portions 23a, 23b are described using reference sign 23, and the pair of second concave portions 24a, 24b are described using reference sign 24. Moreover, in FIG. 7 to FIG. 9, the pair of second convex portions 23a, 23b are each denoted by reference sign 23, and the pair of second concave portions 24a, 24b are each denoted by reference sign 24.

As illustrated in FIG. 7 and FIG. 8, the pair of second convex portions 23 of the present embodiment each include a second peripheral portion 28 serving as a second pivoting surface. On the other hand, the pair of second concave portions 24 each include a second inner circumferential portion 29 that is opposed to the second peripheral portion 28 placed in the concave portion 24 to serve as a sliding surface.

Now, a configuration for achieving a reduction in length of the bending piece set 15 and a reduction in bending radius of the bending portion 13 is described.

In the bending piece set 15, in order to enhance a strength near the engagement portions of the bending pieces, the engagement portions 20 are respectively provided in the thick portions 19a as described above. Then, in the present embodiment, the second convex portions 23 and the second concave portions 24 are configured as described below, whereby a reduction in length of the bending piece set 15 and a reduction in bending radius of the bending portion 13 are realized.

In the present embodiment, a bottom surface of each second concave portion 24 is formed as a reinforcing portion 30 that secures a strength of the middle bending piece 19. The reinforcing portion 30 is a second reinforcing portion. The reinforcing portion 30 has a planar surface 30p parallel to an orthogonal line LL orthogonal to a reference line LC. The reference line LC passes through a central point Cp that is the centers of the first convex portion 21 and the first concave portion 22, and is parallel to the central axis of the rigid pipe.

As a result of forming the planar surface 30p of the reinforcing portion 30 parallel to the orthogonal line LL, a piece width on an engagement portion proximal end side of the middle bending piece 19 becomes a width W3 that can secure a predetermined strength. In conventional cases, the bottom surface of each second concave portion 24 is a concave portion that protrudes to the right in the figure from the orthogonal line LL and includes an inclined planar surface 24p indicated by a broken line. For this reason, in conventional middle bending pieces, part on the bending piece proximal end side is scraped off by the concave portion including the planar surface 24p, and the piece width becomes smaller than the width W3, so that the strength decreases. In the present embodiment, the planar surface 30p is configured by providing a projection portion that fills a space formed by the concave portion including the inclined planar bottom surface 24p in such a conventional case, whereby the piece width is prevented from becoming smaller than the width W3.

On the other hand, an end portion of each second convex portion 23 is provided with a cutout surface 31 and a an escape portion 32. For this reason, the end portion of each second convex portion 23 has a pointed shape.

As illustrated in FIG. 7, the cutout surface 31 is formed as an inclined surface that confronts the planar surface 30p of the reinforcing portion 30 with a predetermined clearance. The cutout surface 31 confronts the planar surface 30p at the time of maximum bending at which the adjacent middle bending pieces 19 are turned with respect to each other about the engagement portion 20 and the distal end-side contact surface 33a and the proximal end-side contact surface 33b come into contact with each other.

That is, an inclination angle of the cutout surface 31 is set in consideration of the maximum bending angle.

Then, a second space S2 is formed between the cutout surface 31 and the planar surface 30p. The second space S2 is secured as a pivot space for enabling the adjacent middle bending pieces 19 to pivot with respect to each other from a linear state to the maximum bent state.

The escape portion 32 prevents the second convex portion 23 from coming into contact with the support portion 26 at the time of the maximum bending. A width size of the support portion 26 can be set to a predetermined size by forming the escape portion 32.

According to these configurations, a size of the piece width on the bending piece proximal end side near the engagement portion 20 can be set to the predetermined width W3 without a change in an amount of pivot between the adjacent middle bending pieces 19. The middle bending piece 19 configured as a result can have a strength high enough to endure a stress caused by tension, compression, torsion, tilting, or the like that acts on the bending portion 13 at the time of bending.

In this way, the engagement portion 20 is configured by the first engagement portion 20A and the second engagement portion 20B. The reinforcing portions 30 are respectively formed in the pair of second concave portions 24 constituting the second engagement portion 20B, and the piece width of the middle bending piece 19 on the proximal end side near the engagement portion 20 is set to the predetermined width W3. As a result, it is possible to realize a configuration of the bending piece set in which: the strength of the middle bending pieces 19 the distance between the pivot axes of which is set to be short is enhanced; and a reduction in entire length and a reduction in bending radius are thus achieved.

Moreover, the planar surfaces 30p are respectively formed in the second concave portions 24, whereas the cutout surfaces 31 are respectively formed in the pair of second convex portions 23. As a result, the distance between the pivot axes of the adjacent middle bending pieces 19 is set to be short, and the amount of pivot between the middle bending pieces 19 can be set to be larger.

Further, an amount of maximum bending between the adjacent middle bending pieces 19 is defined by contact between the distal end-side contact surface 33a and the proximal end-side contact surface 33b. As a result, it is possible to reliably prevent a trouble that scoring occurs on the first pivoting surface and the second pivoting surface or a trouble that the first convex portion 21 and the pair of second convex portions 23 are warped, when a large force directly acts on the engagement portion 20 at the time of the maximum bending.

In the above-mentioned embodiment, because the reinforcing portions 30 each having the planar surface 30p parallel to the orthogonal line are respectively formed in the pair of second concave portions 24 constituting the second engagement portion 20B, the piece width on the bending piece proximal end side is set to the predetermined size, and the strength of the middle bending piece 19 is enhanced.

Figure 10:
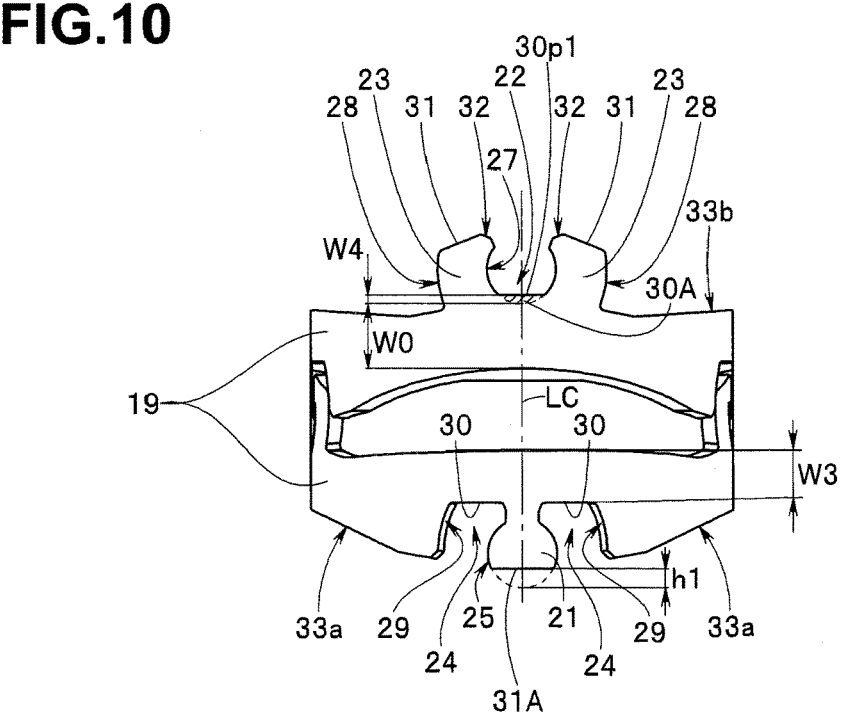
FIG. 10 is a view for describing another configuration of the reinforcing portions of the middle bending pieces.

Alternatively, as illustrated in FIG. 10, the first convex portion 21 may be provided with a cutout surface 31A, and the first concave portion 22 may be provided with a reinforcing portion 30A indicated by hatched lines, whereby the strength of the middle bending pieces 19 the distance between the pivot axes of which is set to be short may be reinforced.

A specific configuration thereof is described.

As illustrated in FIG. 10, the cutout surface 31A is provided on a distal end side of the first convex portion 21. The cutout surface 31A is a first cutout surface. The cutout surface 31A is formed by removing part of the first convex portion 21 from a distal end thereof by a predetermined size h1 as indicated by a broken line. The cutout surface 31A is a planar surface orthogonal to the reference line LC.

The size h1 is a value for making the first peripheral portion 25 smaller within a range in which a bending angle between the adjacent middle bending pieces 19 is not hindered.

The reinforcing portion 30A of the first concave portion 22 is a first reinforcing portion. The reinforcing portion 30A is a projection portion that makes the piece width on the distal end side near the engagement portion 20 wider (larger) by a width W4 from a piece width W0 in an initial state. More specifically, the reinforcing portion 30A is a projection that protrudes from a circular planar surface of the first concave portion 22 in an initial state to change a bottom portion of the concave portion 22 to a flat-bottomed planar surface 30p1. The flat-bottomed planar surface 30p1 of the reinforcing portion 30A is provided at a position away by W4 from a lowermost point of the circular bottom portion of the first concave portion 22. The reinforcing portion 30A reinforces a hatched part that is illustrated in the figure with the width size on the distal end side near the engagement portion 20 being made larger by W4.

Figure 11:
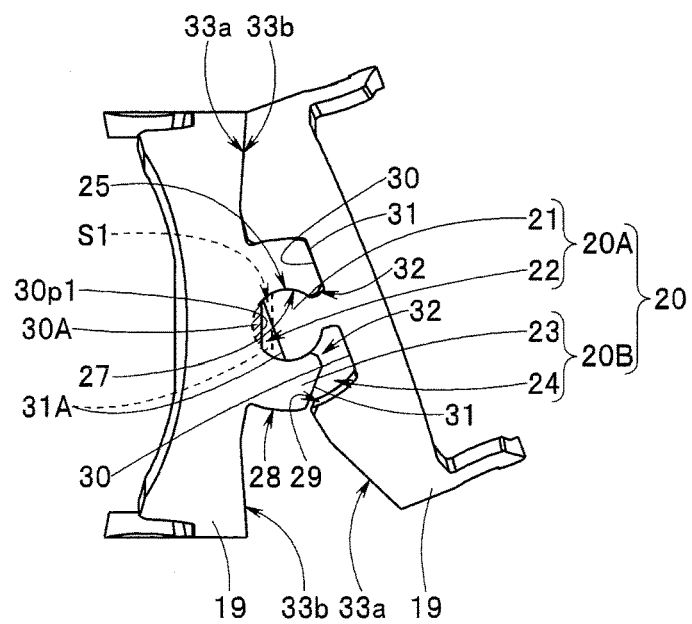
FIG. 11 is a view for describing a state where the adjacent middle bending pieces in FIG. 10 are maximally bent.

The reinforcing portion 30A includes the flat-bottomed planar surface 30p1. The flat-bottomed planar surface 30p1 is a planar surface orthogonal to the reference line LC. Then, when the bending piece set 15 is arranged in the linear state, each flat-bottomed planar surface 30p1 is placed so as to face and be opposed to each cutout surface 31A as indicated by a broken line in FIG. 11. At this time, a first space S1 is formed between the flat-bottomed planar surface 30p1 and the cutout surface 31A.

The first space S1 is a pivot space for enabling the adjacent middle bending pieces 19 to pivot with respect to each other from the linear state to the maximum bent state. In the present embodiment, at the time of the maximum bending at which the distal end-side contact surface 33a and the proximal end-side contact surface 33b come into contact with each other, an end of the cutout surface 31A is away by a predetermined distance from the flat-bottomed planar surface 30p1 of the reinforcing portion 30A without coming into contact therewith.

As a result, similarly to the above, it is possible to reliably prevent a trouble that scoring occurs on the first pivoting surface and the second pivoting surface or a trouble that the first convex portion 21 and the pair of second convex portions 23 are warped, when a large force directly acts on the engagement portion 20 at the time of the maximum bending.

In this way, the pivot space is provided such that the adjacent middle bending pieces 19 can pivot with respect to each other up to a predetermined angle, and the first concave portion 22 is provided with the reinforcing portion 30A, whereby the middle bending piece 19 can be reinforced.

Then, the middle bending piece 19 is provided with the reinforcing portions 30, 30A, whereby the middle bending piece 19 can be more reinforced and the strength thereof can be enhanced.

In the above-mentioned embodiment, the reinforcing portion 30A that is the first reinforcing portion is provided with the flat-bottomed planar surface 30p1 that faces the cutout surface 31A provided on the distal end side of the first convex portion 21.

Figure 12:
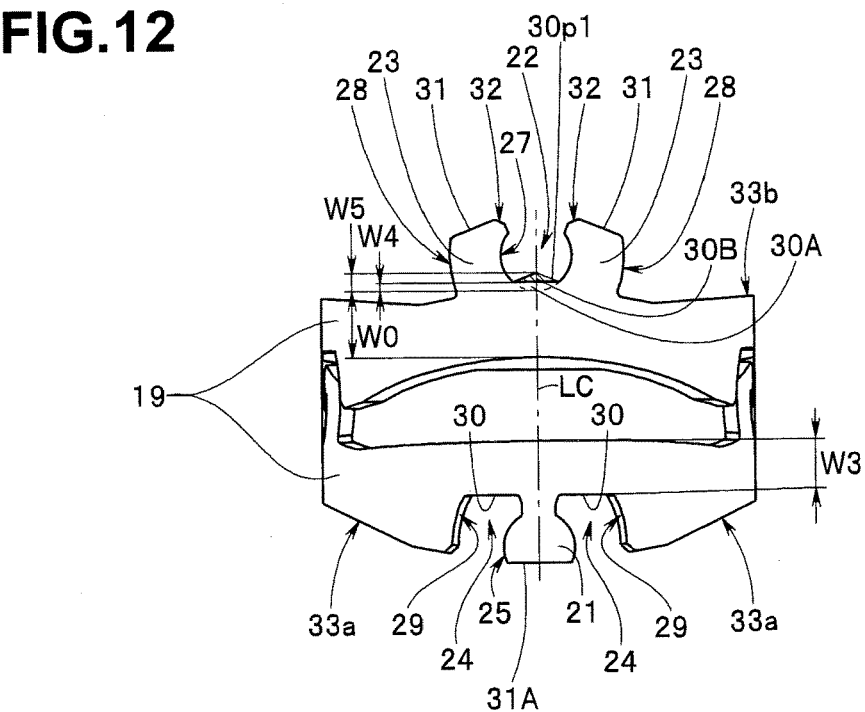
FIG. 12 is a view for describing another configuration of the reinforcing portions of the middle bending pieces.
Figure 13:
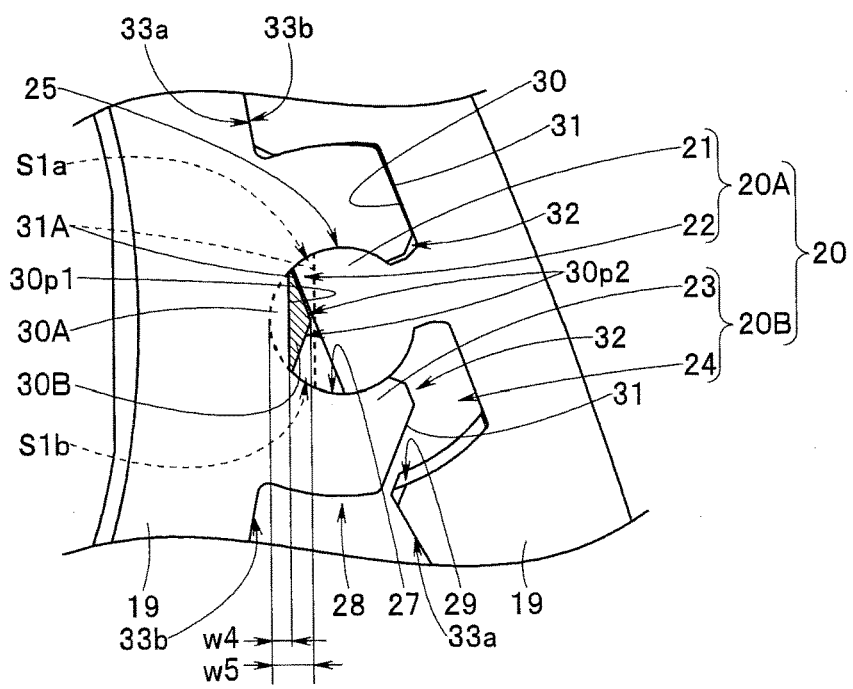
FIG. 13 is a view for describing a state where the adjacent middle bending pieces in FIG. 12 are maximally bent.

Alternatively, without a change in shape of the cutout surface 31A, the reinforcing portion 30A having the flat-bottomed planar surface 30p1 may be further provided with a reinforcing portion 30B including a substantially triangular projection portion illustrated in FIG. 12 and FIG. 13, whereby the first reinforcing portion may be configured.

As illustrated in FIG. 12 and FIG. 13, the reinforcing portion 30B is a second projection portion, and is configured so as to further protrude from the flat-bottomed planar surface 30p1 of the reinforcing portion 30A. The second projection portion has a pair of inclined surfaces 30p2 that respectively extend from both ends of the flat-bottomed planar surface 30p1 toward an opening side of the first concave portion 22. An apex that is an intersection point between the inclined surfaces 30p2 is located on the opening side of the first concave portion 22. As a result, a triangular hatched part illustrated in the figures is a convex portion. An apex of the triangular hatched part is located at W5 that is farther than W4 from the lowermost point of the circular bottom portion of the first concave portion 22. As a result, the width size on the distal end side near the engagement portion 20 is further larger by a size (W5-W4). Note that reference signs S1a, S1b denote pivot spaces for enabling the adjacent middle bending pieces 19 to pivot with respect to each other from the linear state to the maximum bent state.

The pair of inclined surfaces 30p2 have shapes symmetrical to the reference line LC. Inclination angles of the inclined surfaces 30p2 are set in consideration of pivot angles of the adjacent middle bending pieces 19. In the present embodiment, at the time of the maximum bending at which the distal end-side contact surface 33a and the proximal end-side contact surface 33b come into contact with each other, as illustrated in FIG. 13, the cutout surface 31A is away by a predetermined distance from the inclined surfaces 30p2 without coming into contact therewith, and faces one or the other of the inclined surfaces 30p2. As a result, similarly to the above, it is possible to reliably prevent a trouble that scoring occurs on the first pivoting surface and the second pivoting surface or a trouble that the first convex portion 21 and the pair of second convex portions 23 are warped, when a large force directly acts on the engagement portion 20 at the time of the maximum bending.

Note that, in the above-mentioned embodiment, the cutout surface 31A having the planar surface is provided on the distal end side of the first convex portion 21, and the first concave portion 22 is provided with the reinforcing portion 30A having the flat-bottomed planar surface 30p1, whereby the strength of the middle bending piece 19 is enhanced. Alternatively, the first concave portion 22 is further provided with the reinforcing portion 30B including the pair of inclined surfaces 30p2, whereby the strength of the middle bending piece 19 is enhanced.

Figure 14:
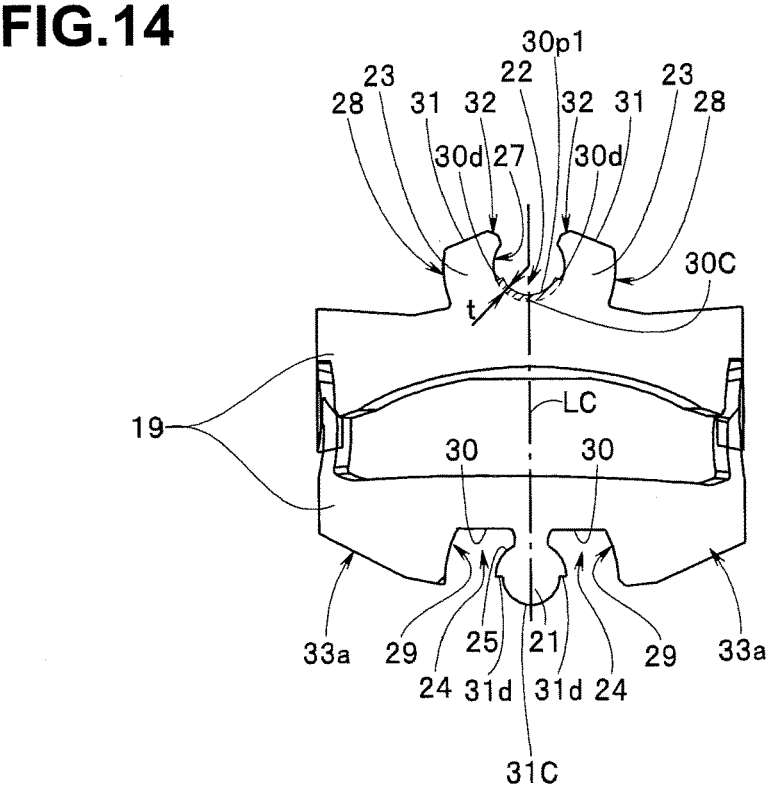
FIG. 14 is a view for describing still another configuration of the reinforcing portions of the middle bending pieces.

Alternatively, instead of providing the first convex portion 21 with the cutout surface 31A having the planar surface, a reinforcing portion 30C illustrated in FIG. 14 may be provided, whereby the strength of the middle bending piece 19 may be reinforced. The first convex portion 21 is provided with a cutout surface 31C having a curved surface, and the first concave portion 22 is provided with the reinforcing portion 30C. The reinforcing portion 30C is configured as a circumferential projection portion that has a concave curved surface indicated by hatched lines and doubles as a sliding surface while being opposed to the cutout surface 31C having the curved surface.

Figure 15:
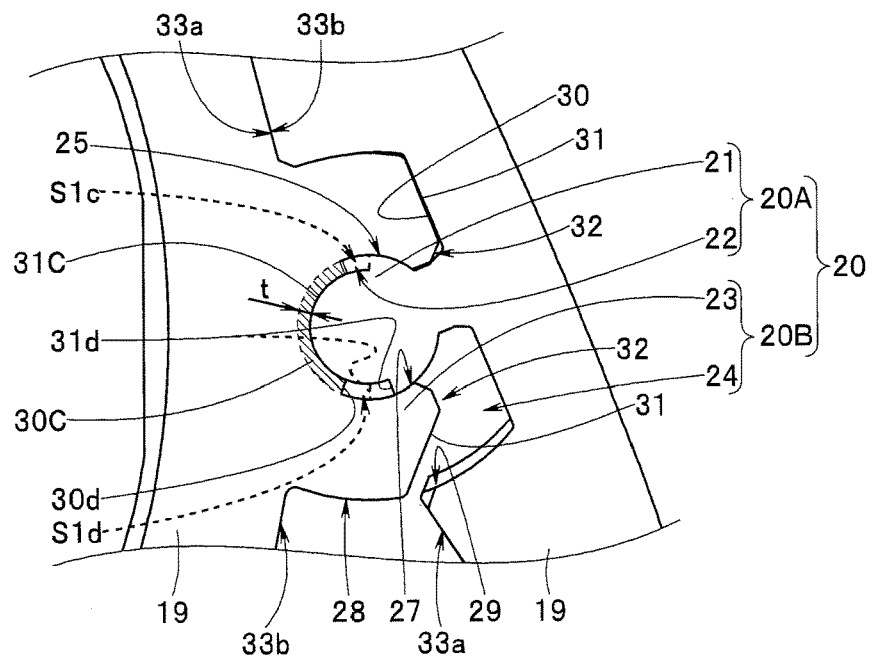
FIG. 15 is a view for describing a state where the adjacent middle bending pieces in FIG. 14 are maximally bent.

More specifically, as illustrated in FIG. 14 and FIG. 15, the cutout surface 31C configured as a concave portion with which the reinforcing portion 30C engages is provided on the distal end side of the first convex portion 21. The cutout surface 31C is the first cutout surface, and is formed by removing part of the first peripheral portion 25 in a predetermined range by a size t that is a predetermined size. The removal range for forming the cutout surface 31C is a range in which the bending angle between the adjacent middle bending pieces 19 is not hindered.

In the present embodiment, a pair of cutout end faces 31d are formed in the cutout surface 31C at positions symmetrical to the reference line LC. In the present embodiment, the cutout end faces 31d are formed in a direction orthogonal to the reference line LC.

The reinforcing portion 30C of the first concave portion 22 is the first reinforcing portion. The reinforcing portion 30C is formed as a projection that protrudes from the first inner circumferential portion 27 in a predetermined range by the size t that is the predetermined size. A formation range of the reinforcing portion 30C is a range in which the bending angle between the adjacent middle bending pieces 19 is not hindered. In the present embodiment, convex portion end faces 30d are formed in the reinforcing portion 30C at positions symmetrical to the reference line LC.

In the present embodiment, the reinforcing portion 30C that is the circumferential projection is provided on a bottom surface side of the second concave portion 22 constituting the middle bending piece 19, whereby the reinforcement of the middle bending piece 19 can be realized.

Note that reference signs S1c, S1d in FIG. 15 denote pivot spaces for enabling the adjacent middle bending pieces 19 to pivot with respect to each other from the linear state to the maximum bent state. As illustrated in the figure, each pivot space is formed between the convex portion end face 30d and the cutout end face 31d.

Then, at the time of the maximum bending at which the distal end-side contact surface 33a and the proximal end-side contact surface 33b come into contact with each other, as illustrated in the figure, the cutout end face 31d faces the convex portion end face 30d so as to be away by a predetermined distance therefrom, without coming into contact therewith.

Consequently, as described above, it is possible to reliably prevent a trouble that scoring occurs on the first pivoting surface and the second pivoting surface or a trouble that the first convex portion 21 and the pair of second convex portions 23 are warped, when a large force directly acts on the engagement portion 20 at the time of the maximum bending.

In the above-mentioned embodiment, in order to achieve a reduction in length of the bending piece set 15 and a reduction in bending radius of the bending portion 13, the bottom surface of each second concave portion 24 is configured as the planar surface 30p parallel to the orthogonal line LL, and the width size on the bending piece proximal end side is set to the predetermined width W3, whereby strength enhancement of the middle bending piece 19 is realized.

If further strength enhancement of the middle bending piece 19 is achieved, a further reduction in length of the bending piece set 15 and a reduction in bending radius of the bending portion 13 can be more easily realized.

Now, a configuration of the second convex portions 23 and the second concave portions 24 of the middle bending piece 19 is described with reference to FIG. 16 to FIG. 17C.

Figure 16:
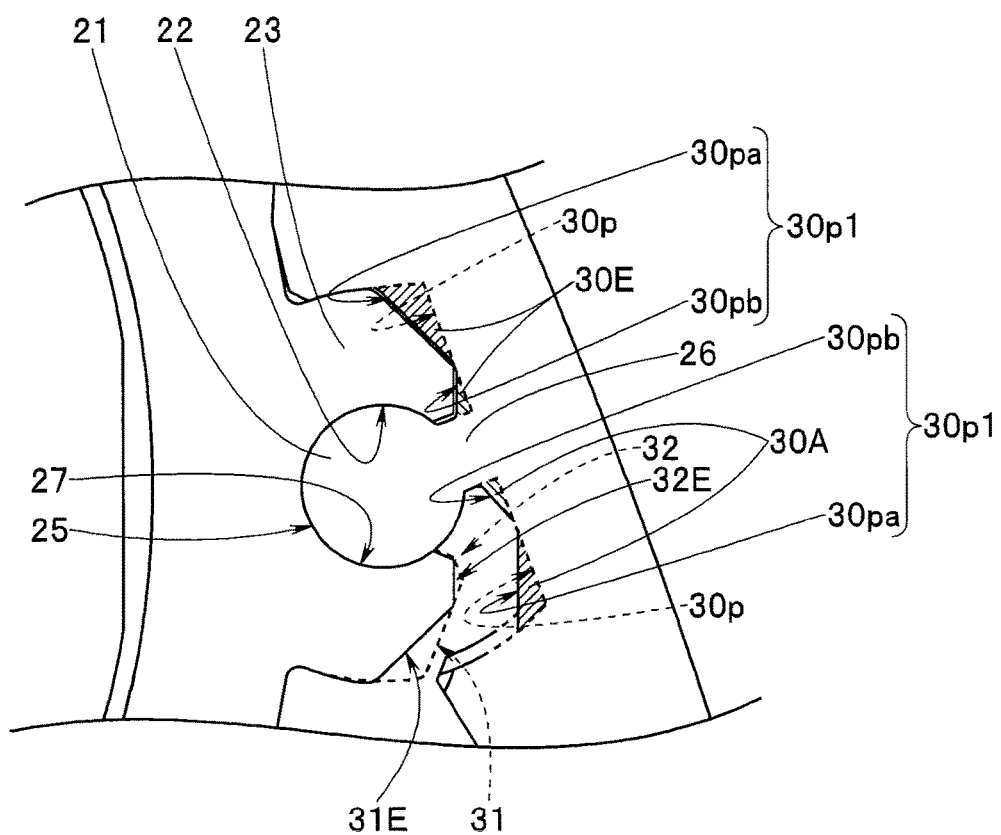
FIG. 16 is a view for describing a middle bending piece including: second concave portions each including a convex portion that forms a V-shaped bottom portion; and second convex portions each including a pointed portion placed in a recess of the convex portion.

In the present embodiment, as illustrated in FIG. 16, each second concave portion 24 includes projection portions 30E that protrude from the planar surface 30p. The bottom surface of the second concave portion 24 is a V-shaped bottom portion 30p1 including a V-shaped recess.

The V-shaped bottom portion 30p1 includes a first inclined surface 30pa and a second inclined surface 30pb. A deepest part of the recess is an intersection point between the first inclined surface 30pa and the second inclined surface 30pb. The deepest part of the recess is located on the planar surface 30p or on an opening side of the second concave portion 24 from the planar surface 30p. That is, when the intersection point is located on the planar surface 30p, the V-shaped bottom surface is configured by the two projection portions 30E having two triangular shapes indicated by hatched lines.

The end portion of each second convex portion 23 is a pointed portion having an outer surface that is placed so as to face the V-shaped bottom portion 30p1 at the time of the maximum bending. The outer surface of the pointed portion is configured by a cutout surface 31E and an escape portion 32E. The cutout surface 31E makes the second peripheral portion 28 smaller within a range in which the bending angle between the adjacent middle bending pieces 19 is not hindered. The escape portion 32E is placed so as to face a side surface 26s of the support portion 26 at the time of the maximum bending.

In this way, the end portion of the second convex portion 23 is provided with the pointed portion configured by: the cutout surface 31E that makes the second peripheral portion 28 smaller within a range in which the bending angle between the adjacent middle bending pieces 19 is not hindered; and the escape portion 32E that faces the side surface 26s of the support portion 26 at the time of the maximum bending. On the other hand, the second concave portion 24 is provided with the projection portions 30E that protrude from the planar surface 30p, the projection portions 30E including the recess having an inner surface that faces the outer surface of the pointed portion.

As a result, the width size on the bending piece proximal end side of the middle bending piece 19 is made larger toward the opening side of the second concave portion 24 by the projection portions 30E that protrude from the planar surface 30p, whereby further strength enhancement of the bending piece 19 can be achieved. That is, the projection portions 30E are reinforcing portions.

Note that, in the above-mentioned embodiment, in order to make the width size on the bending piece proximal end side of the middle bending piece 19 larger toward the opening side of the second concave portion 24, the V-shaped bottom portion 30p1 having the first inclined surface 30pa and the second inclined surface 30pb is formed in the second concave portion 24, whereby the projection portions 30E are provided.

Figure 17A:
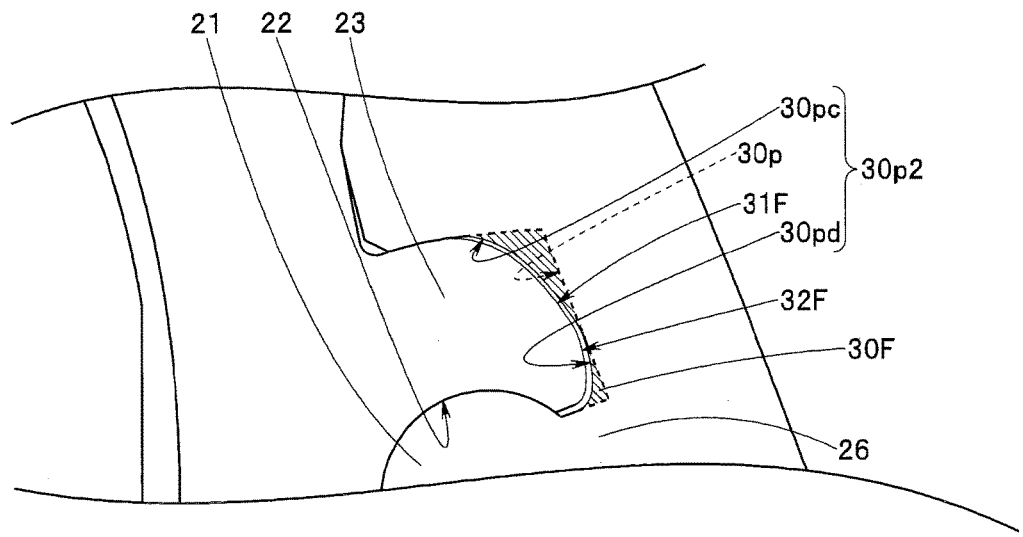
FIG. 17A is a view for describing a middle bending piece including: second concave portions each including a convex portion that forms a U-shaped bottom portion; and second convex portions each including a pointed portion placed in a recess of the convex portion.
Figure 17B:
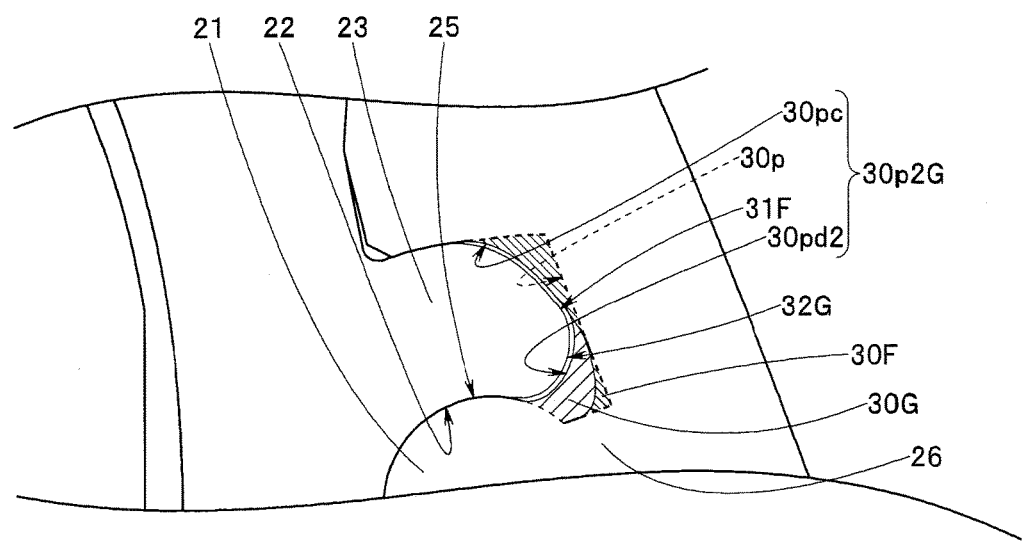
FIG. 17B is a view for describing a middle bending piece including: second concave portions each including a convex portion that forms a second U-shaped bottom portion; and second convex portions each including a pointed portion placed in a recess of the convex portion.
Figure 17C:
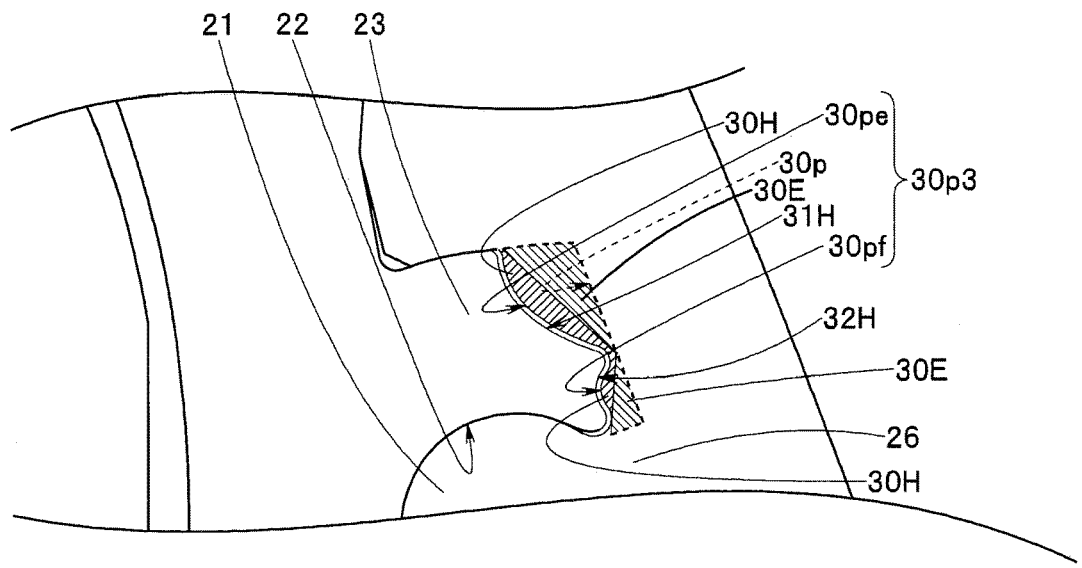
FIG. 17C is a view for describing a middle bending piece including: second concave portions each including a convex portion that forms a concave bottom portion; and second convex portions each including a pointed portion placed in a recess of the convex portion.

The bottom surface of the second concave portion 24 however is not limited to the V-shaped bottom portion 30p1, and may be configured as illustrated in FIG. 17A, FIG. 17B, and FIG. 17C, whereby strength enhancement of the middle bending piece 19 may be achieved.

Projection portions 30F illustrated in FIG. 17A are convex portions that protrude from the planar surface 30p, define a concave curved bottom surface, and are indicated by hatched lines. In the present embodiment, the bottom surface of the second concave portion 24 is a U-shaped bottom portion 30p2 including a flattened U-shaped recess. The U-shaped bottom portion 30p2 has a first concave curved surface 30pc and a second concave curved surface 30pd. The first concave curved surface 30pc is provided in place of the first inclined surface 30pa, and the second concave curved surface 30pd is provided in place of the second inclined surface 30pb. A deepest part of the U-shaped bottom portion 30p2 is an intersection point between the first concave curved surface 30pc and the second concave curved surface 30pd, and the deepest part is located on the planar surface 30p or on the opening side of the second concave portion 24 from the planar surface 30p.

The end portion of the second convex portion 23 is a pointed portion having an outer surface that is placed so as to face the U-shaped bottom portion 30p2. The outer surface of the pointed portion is configured by a cutout convex curved surface 31F and an escape curved portion 32F. The cutout convex curved surface 31F makes the second peripheral portion 28 smaller within a range in which the bending angle between the adjacent middle bending pieces 19 is not hindered. The escape curved portion 32F is placed so as to face the side surface 26s of the support portion 26 at the time of the maximum bending.

According to this configuration, the projection portion 30F is provided so as to protrude from the planar surface 30p, and the width size on the bending piece proximal end side of the middle bending piece 19 is made larger toward the opening side of the second concave portion 24, whereby further strength enhancement of the bending piece 19 can be achieved.

Note that, instead of providing the second concave curved surface 30pd to configure the U-shaped bottom portion 30p2 as described above, as illustrated in FIG. 17B, a second curved surface 30pd2 may be provided. The second curved surface 30pd2 makes the first peripheral portion 25 smaller within a range in which the bending angle between the adjacent middle bending pieces 19 is not hindered. Consequently, a concave curved bottom surface that defines a second U-shaped bottom portion 30p2G having a shape different from a shape of the recess of the U-shaped bottom portion 30p2 is formed in the second concave portion 24. At this time, a pointed portion having an outer surface that faces the second U-shaped bottom portion 30p2G is formed in the end portion of the second convex portion 23. The outer surface of the pointed portion is configured by the cutout convex curved surface 31F and an escape curved portion 32G that faces the second curved surface 30pd2.

According to this configuration, in addition to the projection portions 30F, a projection portion 30G is provided so as to protrude from the planar surface 30p, and the width size on the bending piece proximal end side of the middle bending piece 19 is made further larger toward the opening side of the second concave portion 24, whereby further strength enhancement of the bending piece 19 can be achieved.

Moreover, in FIG. 17A, the U-shaped bottom portion 30p2 configured by the first concave curved surface 30pc and the second concave curved surface 30pd is defined as the bottom surface of the second concave portion 24. Alternatively, as illustrated in FIG. 17C, a concave bottom portion 30p3 configured by a first convex curved surface 30pe and a second convex curved surface 30pf may be defined as the concave curved bottom surface of the second concave portion 24. The first convex curved surface 30pe is provided in place of the first inclined surface 30pa, and the second convex curved surface 30pf is provided in place of the second inclined surface 30pb.

Projection portions 30H illustrated in FIG. 17C are convex portions that respectively protrude from the first inclined surface 30pa and the second inclined surface 30pb constituting the projection portions 30E.

In the present embodiment, the outer surface of the pointed portion of the second convex portion 23 is placed so as to face the concave bottom portion 30p3 at the time of the maximum bending. The outer surface of the pointed portion of the second convex portion 23 is configured by a cutout concave curved surface 31H and an escape curved portion 32H. A deepest part of the concave bottom portion 30p3 is an intersection point between the first convex curved surface 30pe and the second convex curved surface 30pf, and the deepest part is located on the planar surface 30p or on the opening side of the second concave portion 24 from the planar surface 30p.

Note that the cutout concave curved surface 31H makes the second peripheral portion 28 smaller within a range in which the bending angle between the adjacent middle bending pieces 19 is not hindered. The escape curved portion 32H is placed so as to face the side surface 26s of the support portion 26 at the time of the maximum bending.

According to this configuration, the projection portions 30H are provided so as to protrude from the planar surface 30p, and the width size on the bending piece proximal end side of the middle bending piece 19 is made larger toward the opening side of the second concave portion 24, whereby further strength enhancement of the bending piece 19 can be achieved.

Figure 18:
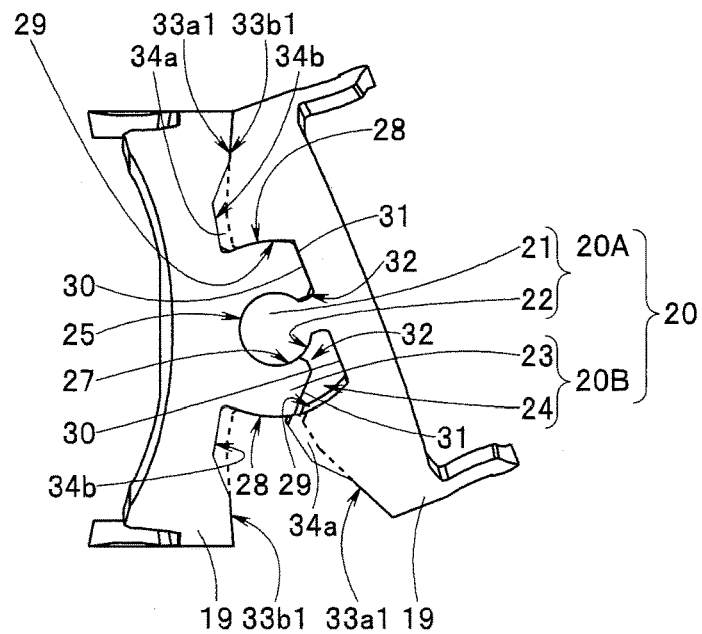
FIG. 18 is a view illustrating adjacent middle bending pieces that are different in configurations of a distal end-side contact surface and a proximal end-side contact surface.

As illustrated in FIG. 17A to FIG. 18 and the like, the recess shape of the bottom surface of the second concave portion 24 and the pointed portion shape of the end portion of the second convex portion 23 are complementary to each other, and the recess inner surface and the pointed portion outer surface face each other at the time of the maximum bending.

In this way, the end portion of the second convex portion 23 is provided with the pointed portion configured by: the cutout surface 31E, 31F, 31H that makes the second peripheral portion 28 smaller within a range in which the bending angle between the middle bending pieces 19 is not hindered; and the escape portion 32E, 32F, 32G, 32H. On the other hand, the second concave portion 24 is provided with the projection portions 30E, 30F, 30F and 30G, 30l1 having the recess complementary to the pointed portion.

As a result, a convex portion that protrudes from a rear surface 19B of the middle bending piece 19 does not need to be provided on the rear surface 19B side, and the width size on the bending piece proximal end side of the middle bending piece 19 can be set to the predetermined width W3 or more. As a result, strength enhancement of the middle bending piece 19 can be achieved.

Note that, in the above description, at the time of the maximum bending at which the distal end-side contact surface 33a and the proximal end-side contact surface 33b come into contact with each other, the recess inner surface of the bottom surface of the second concave portion 24 and the pointed portion outer surface of the end portion of the second convex portion 23 face each other. Alternatively, at the time of the maximum bending at which the recess inner surface of the bottom surface of the second concave portion 24 and the pointed portion outer surface of the end portion of the second convex portion 23 come into contact with each other, the distal end-side contact surface 33a and the proximal end-side contact surface 33b may face each other. In other words, the maximum bent state may be obtained by bringing the recess inner surface of the bottom surface of the second concave portion 24 and the pointed portion outer surface of the end portion of the second convex portion 23 into contact with each other, instead of bringing the distal end-side contact surface 33a and the proximal end-side contact surface 33b into contact with each other.

Moreover, because the second peripheral portion 28 is made smaller within a range in which the bending angle between the middle bending pieces 19 is not hindered, when the bending piece set 15 is brought into the linear state, the smaller second peripheral portion 28 of the second convex portion 23a confronts the second inner circumferential portion 29 of the second concave portion 24a, and the smaller second peripheral portion 28 of the second convex portion 23b confronts the second inner circumferential portion 29 of the second concave portion 24b. Then, when a bending action of the bending portion 13 is performed, the adjacent middle bending pieces 19 pivot with respect to each other up to the maximum bending angle.

Moreover, even in a state where the first peripheral portion 25 is made smaller within a range in which the bending angle between the middle bending pieces 19 is not hindered, the first inner circumferential portion 27 of the first concave portion 22 and the first peripheral portion 25 of the first convex portion 21 are placed so as to confront each other in at least half a circumference thereof.

In this way, the engagement portion 20 is configured by the first engagement portion 20A and the second engagement portion 20B, and the bottom surfaces of the pair of second concave portions 24 constituting the second engagement portion 20B are provided with the projection portions 30E, 30F, 30G, 30H that protrude from the planar surfaces 30p. As a result, it is possible to realize a configuration of the bending piece set 15 in which: the strength of the middle bending pieces 19 the distance between the pivot axes of which is set to be short is enhanced; and a reduction in entire length and a reduction in bending radius are thus achieved.

Moreover, the amount of maximum bending between the adjacent middle bending pieces 19 is defined by contact between the distal end-side contact surface 33a and the proximal end-side contact surface 33b. As a result, it is possible to reliably prevent a trouble that scoring occurs on the first pivoting surface and the second pivoting surface or a trouble that the first convex portion 21 and the pair of second convex portions 23 are warped, when a large force directly acts on the engagement portion 20 at the time of the maximum bending.

Note that, in the present embodiment, when the adjacent middle bending pieces 19 are in the maximum bent state, the end portion of the second convex portion 23 is located outside of the second concave portion 24. Alternatively, shapes of the distal end-side contact surface 33a and the proximal end-side contact surface 33b (whose original shapes are as indicated by broken lines) may be changed as illustrated in FIG. 18. Thus, when the adjacent middle bending pieces 19 are in the maximum bent state, the end portion of the second convex portion 23 may be placed inside of the second concave portion 24.

In this configuration, a distal end-side contact surface 33a1 includes a protruding convex portion 34a. Then, a proximal end-side contact surface 33b1 includes a housing concave portion 34b that houses the protruding convex portion 34a therein. As a result, the end portion of the second convex portion 23 is placed inside of the second concave portion 24, and the second inner circumferential portion 29 and the second peripheral portion 28 are placed so as to always face each other, so that a smooth bending action of the bending piece set 15 can be obtained.

Moreover, in the present embodiment, the concave locking portions are provided on the distal end side of one middle bending piece 19 so as to be opposed to each other, and the convex locking portions with which the concave locking portions respectively engage are provided on the proximal end side thereof so as to be opposed to each other. Alternatively, the bending piece set 15 may be configured by alternately placing: a first middle bending piece provided with the concave locking portions on the distal end side and the proximal end side thereof; and a second middle bending piece provided with the convex locking portions on the distal end side and the proximal end side thereof.

Now, the engagement portion formed by a laser beam is described.

Figure 19:
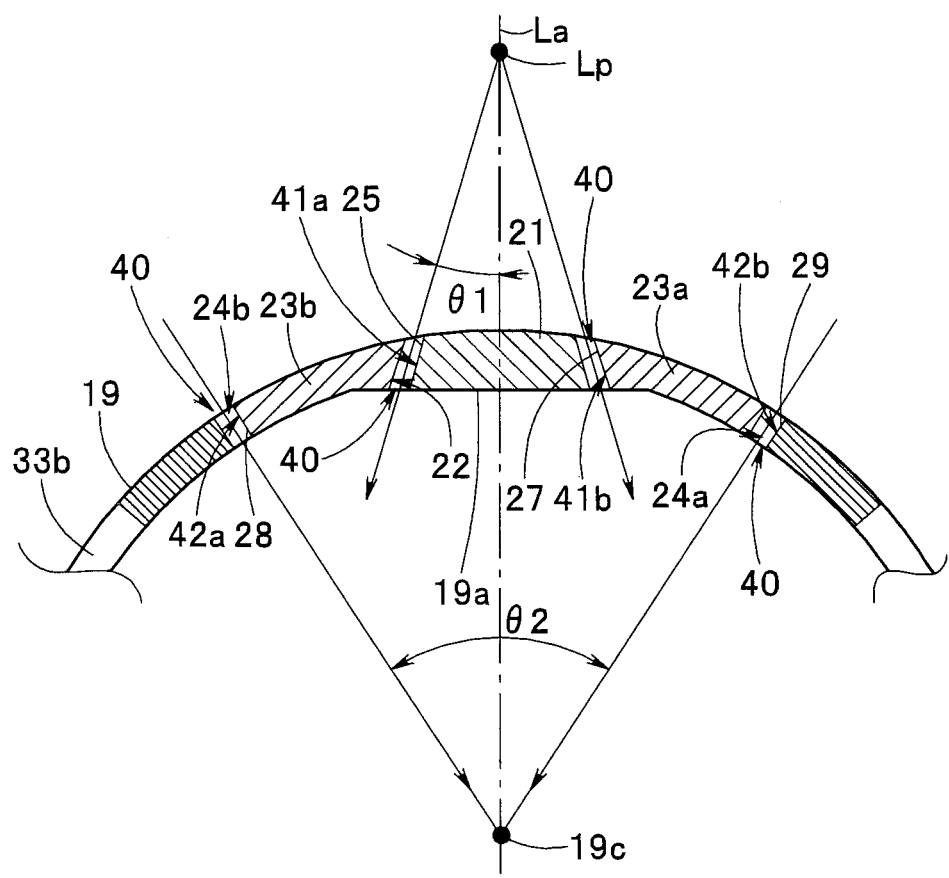
FIG. 19 is a schematic view for describing tapered surfaces that are formed on a rigid pipe by a laser beam as well as a relation among second peripheral portions of a pair of second convex portions, a first peripheral portion of a first convex portion, and second inner circumferential portions of a pair of second concave portions.

When the first convex portion 21 and the first concave portion 22 constituting the engagement portion 20 are formed by cutting with a laser beam, as illustrated in FIG. 19, the laser beam is emitted at a predetermined angle θ1 from a predetermined laser beam emission point Lp outside of the middle bending piece 19. As a result, a first tapered surface 41a having a taper angle 2θ1 is formed in the first peripheral portion 25 of the first convex portion 21, and the first tapered surface 41a is part of a conical shape whose apex is the laser beam emission point Lp. A first tapered surface 41b having the taper angle 2θ1 is similarly formed in the first inner circumferential portion 27 of the first concave portion 22.

In this configuration, the first tapered surface 41a is a tapered surface having an outer diameter size that continuously becomes smaller from the bending piece inner surface side toward the bending piece outer surface side. On the other hand, the first tapered surface 41b is a tapered surface having an inner diameter size that continuously becomes smaller from the bending piece outer surface side toward the bending piece inner surface side.

The laser beam emission point Lp is at a position away by a predetermined distance from the bending piece 19, on a virtual line La passing through a central axis of the middle bending piece 19 and a center of the first convex portion.

On the other hand, when the second convex portion 23a and the second concave portion 24a as well as the second convex portion 23b and the second concave portion 24b are formed by cutting with a laser beam, as illustrated in the figure, the laser beam emitted from an emission point (not illustrated) outside of the middle bending piece 19 travels toward a center 19c of the bending piece 19. As a result, a second tapered surface 42a having a taper angle θ2 is formed in each of the second peripheral portions 28 of the second convex portions 23a, 23b, and the second tapered surface 42a is part of a conical shape whose apex is the center 19c of the middle bending piece 19. Moreover, a second tapered surface 42b having the taper angle θ2 is similarly formed in each of the second inner circumferential portions 29 of the second concave portions 24a, 24b.

In this configuration, the second tapered surface 42a is a tapered surface having an outer diameter size that continuously becomes smaller from the bending piece outer surface side toward the bending piece inner surface side. On the other hand, the second tapered surface 42b is a tapered surface having an inner diameter size that continuously becomes smaller from the bending piece outer surface side toward the bending piece inner surface side. Reference sign 40 denotes a separation joint.

An action of the engagement portion 20 including the first tapered surfaces 41a, 41b and the second tapered surfaces 42a, 42b as described above is described.

In each of the engagement portions 20 of the adjacent middle bending pieces 19, the first tapered surface 41a is formed in the first peripheral portion 25, and the first tapered surface 41b is formed in the first inner circumferential portion 27, whereby the first convex portion 21 is configured as a receiver portion that supports the first inner circumferential portion 27 constituting the first concave portion 22 of the second convex portions 23a, 23b.

On the other hand, the second tapered surface 42b is formed in each second inner circumferential portion 29, and the second tapered surface 42a is formed in each second peripheral portion 28, whereby the second inner circumferential portions 29 are configured as receiver portions that support the second peripheral portions 28 of the second convex portions 23a, 23b opposed to the second inner circumferential portions 29.

Accordingly, the tapered surface 41b of the second convex portions 23a, 23b constituting the engagement portion 20 is put on the tapered surface 41a of the first peripheral portion 25 of the first convex portion 21, and the tapered surfaces 42a of the second convex portions 23a, 23b constituting the engagement portion 20 are respectively put on the tapered surfaces 42b of the second inner circumferential portions 29 of the second concave portions 24a, 24b.

For this reason, in a case where a tensile force acts on the bending piece set 15, a force that causes the second convex portions 23a, 23b to collapse toward the central axis of the bending piece set 15 is prevented from acting from a surrounding area of the second convex portions 23a, 23b.

As a result, it is possible to solve a trouble that engagement of the engagement portion 20 is cancelled when an excessive tensile force acts on the bending piece set 15.

Note that the rigid pipe is generally made of stainless steel, but may be made of a nickel-titanium alloy. Moreover, the above-mentioned bending portion is configured to be bent in the four directions, but the bending direction of the bending portion is not limited to the four directions, and may be two directions. Further, not limited to a medical endoscope, the bending portion configured as described above is applied to active bending portions for a rigid endoscope with a bending portion, an industrial endoscope, a medical treatment instrument, a medical catheter, and the like, and is also applied to flexible instruments that are passively inflected.

Note that the present invention is not limited only to the above-mentioned embodiment, and various modifications thereof can be carried out within a range not departing from the gist of the present invention.

What is claimed is:

1. A bending portion in which a plurality of bending pieces are pivotably continuously provided, the bending portion comprising:

a first bending piece and a second bending piece provided adjacent to each other;

the first bending piece comprising:

a circular convex portion comprising a peripheral portion having a circular arc shape;

a support portion extended along an axial line direction of the first bending piece from a circular convex portion and supporting the circular convex portion;

a pair of engaging concave portions provided so as to sandwich the circular convex portion and the support portion; and a pair of distal-end-side contact portions respectively extended from the engaging concave portions in an opposite direction of the circular convex portion, the pair of engaging concave portions each comprising:
a first inclined portion extended from the support portion in a direction to form an obtuse angle with the support portion;
a second inclined portion extended from the first inclined portion in a direction to form an obtuse angle with the first inclined portion; and
an inside portion that is bent in an obtuse angle with respect to the second inclined portion and extended along a concentric arc of the peripheral portion so as to be adjacent to the distal-end-side contact portion; and
the second bending piece comprising:
a circular concave portion comprising an inside portion having a circular arc shape configured to slide with respect to the peripheral portion, the circular concave portion being provided so as to be pivotable around the circular convex portion;
a pair of engaging convex portions provided so as to sandwich the circular concave portion; and
a pair of proximal-end-side contact portions respectively extended from the engaging convex portions in an opposite direction from the circular concave portion, the pair of proximal-end-side contact portions being configured to come into contact with the distal-end-side contact portions when the circular concave portion pivots around the circular convex portion,
the pair of engaging convex portions each comprising:
a pair of pointed portions having a shape along the support portion, the first inclined portion, and the second inclined portion, one of the pair of pointed portions being placed at a back of the engaging concave portion to face the support portion, the first inclined portion, and the second inclined portion when the distal-end-side contact portions and the proximal-end-side contact portion contact with each other; and
an outside portion that is bent in an obtuse angle with respect to the pointed portions and extended along a concentric arc of the inside portion so as to be adjacent to the proximal-end-side contact portion.

2. The bending portion according to claim 1, wherein the circular convex portion and the circular concave portion each have an outer diameter that becomes smaller from a bending piece inner surface side toward a bending piece outer surface side.

3. The bending portion according to claim 2, wherein the engaging convex portions and the engaging concave portion each have an outer diameter that becomes smaller from the bending piece outer surface side toward the bending piece inner surface side.

4. The bending portion according to claim 1, wherein the circular convex portion and the circular concave portion confront each other in at least half a circumference thereof.

5. An endoscope comprising:
a bending portion in which a plurality of bending pieces are pivotably continuously provided, the bending portion being provided at a distal end side of the insertion portion configured to be inserted into a living body or a tube,
the bending portion, comprising:

a first bending piece and a second bending piece provided adjacent to each other
the first bending piece comprising:
a circular convex portion comprising a peripheral portion having a circular arc shape;
a support portion extended along an axial line direction of the first bending piece from a circular convex portion and supporting the circular convex portion;
a pair of engaging concave portions provided so as to sandwich the circular convex portion and the support portion; and
a pair of distal-end-side contact portions respectively extended from the engaging concave portions in an opposite direction of the circular convex portion,
the pair of engaging concave portions each comprising:
a first inclined portion extended from the support portion in a direction to form an obtuse angle with the support portion;
a second inclined portion extended from the first inclined portion in a direction to form an obtuse angle with the first inclined portion; and
an inside portion that is bent in an obtuse angle with respect to the second inclined portion and extended along a concentric arc of the peripheral portion so as to be adjacent to the distal-end-side contact portion; and
the second bending piece comprising:
a circular concave portion comprising an inside portion having a circular arc shape configured to slide with respect to the peripheral portion the circular concave portion being provided so as to be pivotable around the circular convex portion;
a pair of engaging convex portions provided so as to sandwich the circular concave portion; and
a pair of proximal-end-side contact portions respectively extended from the engaging convex portions in an opposite direction from the circular concave portion, the pair of proximal-end-side contact portions being configured to come into contact with the distal-end-side contact portions when the circular concave portion pivots around the circular convex portion,
the pair of engaging convex portions each comprising:
a pair of pointed portions having a shape along the support portion, the first inclined portion, and the second inclined portion, one of the pair of pointed portions being placed at a back of the engaging concave portion to face the support portion, the first inclined portion, and the second inclined portion when the distal-end-side contact portions and the proximal-end-side contact portion contact with each other; and
an outside portion that is bent in an obtuse angle with respect to the pointed portions and extended along a concentric arc of the inside portion so as to be adjacent to the proximal-end-side contact portion.

6. The bending portion according to claim 1, wherein
the circular convex portion, the support portion, the engaging concave portion, the circular concave portion, and the engaging convex portion couple one side of the first bending piece and the second bending piece to each other such that the first bending piece and the second bending piece are pivotable in a top-bottom direction, and the circular convex portion, the support portion, the engaging concave portion, the circular concave portion, and the engaging convex portion couple another side of the first bending piece and the second bending piece to each other such that the first bending piece and the second bending piece are pivotable in a left-right direction.

7. The bending portion according to claim 1, wherein the adjacent first bending piece and the second bending piece are formed simultaneously by cutting a rigid pipe.

8. The bending portion according to claim 1, wherein the outside portion and the inside portion includes a part of the circle with the pivot axis as the center, and slide with respect to each other.

9. The bending portion according to claim 7, wherein a rigid pipe for forming the bending piece set includes a thick portion having a thickness larger than a thickness therearound, and includes the circular convex portion, the support portion, the engaging concave portion, the circular concave portion, and the engaging convex portions are in the thick portion.

10. The bending portion according to claim 7, wherein the bending piece set is formed by cutting the rigid pipe through application of a laser beam from an outer circumferential face side of the rigid pipe.

\* \* \* \* \*